(12) United States Patent
Jackson et al.

(10) Patent No.: US 7,527,788 B2
(45) Date of Patent: May 5, 2009

(54) DESATURASE ANTIGEN OF MYCOBACTERIUM TUBERCULOSIS

(75) Inventors: Mary Jackson, Paris (FR); Brigitte Gicquel, Paris (FR)

(73) Assignee: Institut Pasteur, Paris (FR)

( * ) Notice: Subject to any disclaimer, the term of this patent is extended or adjusted under 35 U.S.C. 154(b) by 0 days.

(21) Appl. No.: 11/357,726

(22) Filed: Feb. 21, 2006

(65) Prior Publication Data

US 2006/0241291 A1    Oct. 26, 2006

Related U.S. Application Data

(62) Division of application No. 10/368,433, filed on Feb. 20, 2003, now Pat. No. 7,071,320, which is a division of application No. 09/230,485, filed as application No. PCT/IB97/00923 on Jul. 25, 1997, now Pat. No. 6,582,925.

(60) Provisional application No. 60/022,713, filed on Jul. 26, 1996.

(51) Int. Cl.
*A61K 39/00* (2006.01)
*A61K 39/395* (2006.01)
*A61K 39/40* (2006.01)

(52) U.S. Cl. .............. 424/139.1; 424/130.1; 424/141.1; 424/150.1; 424/164.1; 424/168.1; 424/248.1

(58) Field of Classification Search .............. 424/130.1, 424/139.1, 141.1, 150.1, 164.1, 168.1, 184.1, 424/248.1
See application file for complete search history.

(56) References Cited

U.S. PATENT DOCUMENTS

| 6,010,855 A | 1/2000 | Jackson et al. |
| 6,204,038 B1 | 3/2001 | Jackson et al. |
| 6,248,581 B1 | 6/2001 | Gicquel et al. |

FOREIGN PATENT DOCUMENTS

| WO | WO 92 16652 A | 10/1992 |
| WO | WO 94 00493 A | 1/1994 |
| WO | WO 95 14713 A | 1/1995 |

OTHER PUBLICATIONS

Shanklin, J., et al., Proc. Natl. Acad. Sci., USA, vol. 88, pp. 2510-2514, Mar. 1991.*
Yokohama, W.M., Production of Monoclonal Antibodies, Unit 2.5.1 to 2.5.17, Current Protocols in Immunology, vol. 1, Colgan et al, eds., Wiley & Sons, Inc., NY, 1996.*
Lim et al., "Identification of Mycobacterium Tuberculosis DNA Sequences Encoding Exported Proteins by Using phoA Gene Fusions," J. of Bact., vol. 177, No. 1, pp. 59-65 (1995).
Eiglmeier et al., "Use of an Ordered Cosmid Library to Deduce the Genomic Organization of Mycobacterium Leprae," Embl. seq. data library, Accession No. L78822 (1996).
Jackson et al., Embl. Sequence Data Library, Accession No. U49839 (1996).
Jackson et al., "Mycobacterium Tuberculosis Des Protein: An Immunodominant Target for the Humoral Response of Tuiberculous Patients," Infect. & Immunity, vol. 65, No. 7, pp. 2883-2889 (1997).
U.S. Appl. No. 09/429,370, filed Oct. 28, 1999.
Philipp et al., "An integrated map of the genome of the *Tubercle bacillus*, Mycobacterium tuberculosis H37Rv, and comparison with Mycobacterium leprae", *Proc. Nat'l. Acad. Sci., U.S.A.*, vol. 93, pp. 3132-3137 (1996).
Sequence search, SEQ ID No. 2, ran Apr. 30, 2002.
Results of Blast 2 Sequence Analysis Comparing Applicant's SEQ ID No. 2 to DES sequences 417820 and 134945, from *Cucumis sativus* and *Ricinus communis*.
ProPred MHC Class-II Binding Peptide Prediction Server.
"Antigenic" Motif Report File, run Mar. 26, 2008.
"Antigenic" Program Description, *Annex* 3.
Parker, J.M.R. et al., "New Hydrophilicity Scale Derived from High-Performance Liquid Chromatography Peptide Retention Data: Correlation of Predicted Surface Residues with Antigenicity and X-ray-Derived Accessible Sites," *Biochemistry* 1986, 25, 5425-5432.
Kolaskar, A.S. et al., "A semi-empirical method for prediction of antigenic determinants on protein antigens," *FEBS* 09210, vol. 276, No. 1,2 172-174.
Coligan, John E. et al., "Current Protocols in Immunology," vol. 1.

* cited by examiner

*Primary Examiner*—Rodney P. Swartz
(74) *Attorney, Agent, or Firm*—Finnegan, Henderson, Farabow, Garrett & Dunner, L.L.P.

(57) ABSTRACT

Antibodies that bind to the *M. tuberculosis* Des protein are provided.

4 Claims, 12 Drawing Sheets

SEQ ID NO: 1
1    GATCATCATGGCCGGCTGCCGCGCAGGGCGCCGACACCGGCGCCGAGTGCGGGGCCGAGGATCGGCCCCCAC
71   CAGTTCGGCAGCTGCGTGTCGATGCCGGCTCCACAATCCCGGAAAACAGCTCGACCATTACCTCCTCAATAT
141  GAGCCTCGAAAAACTTGCCGCTGTGCGCGGGCGTCGTGTGAGCGCACACAACAACTGTTAGCTGACCAGC
211  AGGATCGGCGCTCTTACCGGTCTGTTCACCGCCATATCTGAACGGACGGCTGGAGCGCACCCGCAAGCAAT
281  TCATCGACTACTGCGTCAACATGTTGCTCAGCACCCGCCGCCACCTACGCACCGCCACCCGCGAGCGGGAGA
351  ATCCGAACACTCCATCCAGCCGGGCCGCACAACTGAGGACGACTGGGGTTCACCCCAGCGGCCACCGG
421  CGCCCCGCGATGCCAGCATCCTGCCCGTGCTGTGGCAGCTCAACATGCCGCGAAGCCCAAACTTGATGC
491  TACCGAGAGACACAGATATATTGACTGCAACCATTAGACACAGATAACTGAGGCGCCATGTCAGCCAAG
                                                  SEQ ID NO: 2  M  S  A  K
561  CTGACCGACCTGCAGCTGCTGCACGAACTGGTTCGAGAAGTACCTGAACCGGCACCTGAGCA
      L  T  D  L  Q  L  L  H  E  L  E  P  V  V  E  K  Y  L  N  R  H  L  S  M
631  TGCACAAGCCCTGGAACCCGCACGACTACATCCCGTGTCGGTCGGACGGGAAGAACTACTACGCGCTCGGCGG
      H  K  P  W  N  P  H  D  Y  I  P  W  S  D  G  K  N  Y  Y  A  L  G  G
701  GCAGGATTGGGACCCCGACCAGAGCAAGCTTTCTGATGTCGCCCAGGTGGCGATGTGCAGAACCTGGTC
      Q  D  W  D  P  D  Q  S  K  L  S  D  V  A  Q  V  A  M  V  Q  N  L  V
771  ACCGAGGACAACTGCCTCGTATCACCGCGAGATCGCCATGAACATGGGCATGGACGGCGCGTGGGGGC
      T  E  D  N  L  P  S  Y  H  R  E  I  A  M  N  M  G  M  D  G  A  W  G  Q
841  AGTGGGTCAACCGTTGGACCGCCGAGGAGAATCGGCACGGCATCGCTCGACTACCTGGTGGTGAC
      W  V  N  R  W  T  A  E  E  N  R  H  G  I  A  L  R  D  Y  L  V  V  T
911  CCGATCGGTCGACCCTGTCGAGTTGGAGAAACTTCGCCTCGAGGTAGTCAACCGGGCTTCAGCCAGGC
      R  S  V  D  P  V  E  L  E  K  L  R  L  E  V  V  N  R  G  F  S  P  G

```
 981 CAAAACCACCAGGGCCACTATTCGCGGAGAGCCTCACCGACTCGTCCTCTATGTCAGTTTCCAGGAAC
       Q  N  H  Q  G  H  Y  F  A  E  S  L  T  D  S  V  L  Y  V  S  F  Q  E  L
1051 TGGCAACCCGGATTTCGCACCGCAAGGCATGTAACGACCCCGTCGCCGACCAGTCTCATGGC
       A  T  R  I  S  H  R  N  T  G  K  A  C  N  D  P  V  A  D  Q  L  M  A
1121 CAAGATCTCGGCAGACGAGAATCTGCACATGATCTTCTACCGCGACGTCAGCGAGGCCGCGTTCGACCTC
       K  I  S  A  D  E  N  L  H  M  I  F  Y  R  D  V  S  E  A  A  F  D  L
1191 GTGCCAACCAGGCCATGAAGTCGCTGCACCTGATTTTGAGCCACTTCCAGATGCCCGGCTTCCAAGTAC
       V  P  N  Q  A  M  K  S  L  H  L  I  L  S  H  F  Q  M  P  G  F  Q  V  P
1261 CCGAGTTCCGGCGCAAAGCCGTGGTCATCGCCGTCGGGGGTGTCTACGACCCGCGCATCCACCTCGACGA
       E  F  R  R  K  A  V  V  I  A  V  G  G  V  Y  D  P  R  I  H  L  D  E
1331 AGTCGTCATGCCGGTACTGAAGAAATGTATCTTCGAGCGCGAGGACTTCACCGGCGAGGGGCTAAG
       V  V  M  P  V  L  K  K  W  C  I  F  E  R  E  D  F  T  G  E  G  A  K
1401 CTGCGCGACGAGCTGGCCCTGGTGATCAAGGACCTCGAGCTGCCGCACAAGTTCGAGTGTCCAAGC
       L  R  D  E  L  A  L  V  I  K  D  L  E  L  A  C  D  K  F  E  V  S  K  Q
1471 AACGCCAACTCGACGGGGAAGCCGTACGGGCAAGAAGGTCAGCGCACAGAGCTGCATAAAACCGCTGG
       R  Q  L  D  R  E  A  R  T  G  K  K  V  S  A  H  E  L  H  K  T  A  G
1541 CAAACTGGGCGATGAGCCGTCGTTAGCCCGGATGAGCAGGAGGCGGG
       K  L  A  M  S  R  R  *
1611 CAATCCAACCCAGCCCCGGCGATGCAGAGCCGCAGCGCCGATGAGCAGGAGGTGGCAATCCAACCA
1681 GCCCGGCGTTG
```

```
                           ┌─────── Fe_A site ───────┐
         ┌─── B Helix ───┐                    ┌── C Helix ──┐
Ribonucleotide reductases v01555  049  EFYKFLFTFL AMA E KLVNFN IDELVTSFES HDIDHYYTEQKAM ENVH GETYA 099  SEQ ID NO: 5
k02672  072  IFISNLKYQT LL D SIQGRSP NVALLPLISI PELETWETWAFS  ETIH SRSYT 123  SEQ ID NO: 6

Hydrocarbon hydroxylases m58499  102  ETMKVVSNFL EVG E YNAIAA TGMLWDSAQA AEQKNGYLAQVL D EIRH THQCA 152  SEQ ID NO: 7
x55394  102  ETMKVISNFL EVG E YNAIAA SAMLWDSATA AEQKNGYLAQVL D EIRH THQCA 152  SEQ ID NO: 8
m60276  097  NALKLFLTAV SPL E YQAFQG FSRVGRQFSG AGARVACQMQAI D ELRH VQTQV 147  SEQ ID NO: 9
m65106  092  STLKSHYGAI AVG E YAAVTG EGRMARFSKA PGNRNMATFGMM D ELRH GQLQL 142  SEQ ID NO: 10

Stearoyl-ACP-desaturases m59857  133  LVGDMITEEA LPTYQTMLNT LDGVRDETGA SPTSWAIWTRAWTA E ENRH GDLLN 184  SEQ ID NO: 11
m59858  133  LVGDMITEEA LPTYQTMLNT LDGVRDETGA SPTPWAIWTRAWTA E ENRH GDLLN 184  SEQ ID NO: 12
m61109  133  LVGDMITEEA LPTYQTMLNT LDGVRDETGA SLTPWAVWTRAWTA E ENRH GDLLH 184  SEQ ID NO: 13
x62898  136  LVGDMITEEA LPTYQTMLNT LDGAKDETGA SPTSWAVWTRAWTA E ENRH GDLLN 187  SEQ ID NO: 14
x60978  135  LVGDMITEEA LPTYQTMLNT LDGVRDETGA SPTSWAIWTRAWTA E ENRH GDLLN 186  SEQ ID NO: 15
m91238  130  LIGDMITEEA LPTYQTMINT LDGVRDETGA TVTPWAIATRAWTA E ENRH GDLLN 181  SEQ ID NO: 16
x70962  133  LVGDMITEEA LPTYQTMINT LDGVRDETGA SLTPWAIWTRAWTA E ENRH GDLLN 184  SEQ ID NO: 17
m93115  121  LVGDMITEEA LPTYMSMLNR CDGIKDDTGA QPTSWATWTRAWTA E ENRH GDLLN 172  SEQ ID NO: 18

M. tuberculosis DES protein

Mtb.des  062  SDVAQVAMVQ NLVTEDNLPS YHREIAMNMG MDGAWGQWVNRWTA E ENRH GIALR 115  SEQ ID NO: 33
```

FIG. 3A $Fe_B$ site

E Helix F Helix

Ribonucleotide reductases v01555 145 EKILVFLLI E GIFFISSFYS IALLRVRGLM PGICLANNYISR D ELLH TRAAS 196 SEQ ID NO: 19
k02672 195 LCLMSVNAL E AIRFYVSFAC SFAFAERELM EGNAKIIRLIAR D EALH LTGTQ 246 SEQ ID NO: 20

Hydrocarbon hydroxylases m58499 200 CSLNLQLVG E ACFTNPLIVA VTEWAAANGD EITPTVFLSIET D ELRH MANGY 251 SEQ ID NO: 21
X55394 200 CSVNLQLVG D TCFTNPLIVA VTEWAIGNGD EITPTVFLSVET D ELRH MANGY 251 SEQ ID NO: 22
m60276 191 FLTAVSFSF E YVLTNLLFVP FMSGAAYNGD MATVTFGFSAQS D EARH MTLGL 242 SEQ ID NO: 23
m65106 188 VAIMLTFSF E TGFTNMQFLG LAADAAEAGD YTFANLISSIQT D ESRH AQQGG 239 SEQ ID NO: 24

Stearoyl-ACP-desaturases m59857 219 YLGFIYTSFQ E RATFISHGN TARQAKEHGD IKLAQICGTIAA D EKRH ETAYT 270 SEQ ID NO: 25
m59858 219 YLGFIYTSFQ E RATFISHGN TARLAKEHGD IKLAQICGTITA D EKRH ETAYT 270 SEQ ID NO: 26
m61109 219 YLGFIYTSFQ E RATFVSHGN TARHAKDHGD VKLAQICGTIAS D EKRH ETAYT 270 SEQ ID NO: 27
x62898 222 YLGFVYTSFQ E RATFVSHGN SARLAKEHGD LKMAQICGIIAS D EKRH ETAYT 273 SEQ ID NO: 28
x60978 221 YLGFIYTSFQ E RATFISHGN TARQAKEHGD LKLAQICGTIAA D EKRH ETAYT 272 SEQ ID NO: 29
m91238 216 YLGFVYTSLR K GVTFVSHGN TARLAKEHGD MKLAQICGSIAA D EKRH ETAYT 267 SEQ ID NO: 30
x70962 219 YLGFIYTSFQ E RATFISHGN TARLAKDHGD MKLAQICGIIAA D EKRH ETAYT 219 SEQ ID NO: 31
m93115 207 YMGFIYTSFQ E RATFISHAN TAKLAQHYGD KNLAQVCGNIAS D EKRH ATAYT 258 SEQ ID NO: 32

M. tuberculosis DES protein

Mtb. des 157 TDSVLYVSFQ E LATRISHRN TGKACNDPVA DQLMAK...ISA D ENLH MIFYR 205 SEQ ID NO: 34

—□— Average of tuberculous patients
(*M. tuberculosis*) (15 individuals)

—◇— Average of tuberculous patients
(*M. bovis*) (5 individuals)

---○--- Average of non-tuberculous patients
(24 individuals)

```
  1  GATCATCATCGGCCGGCTGCCGCGCAGGGCGCCGACACCGGCGAGTGCGGGGCGGAGGATCGGCCCCCAC
 71  CAGTTCGGGCAGCTGCGTGTCGATGCGCTCCACAATCCCGGGAAACAGCTCGACCATTACCTCCTCAATAT
141  GAGCCTCGAAAAACTTGCCGCTGTGCGCGGCGTCGTGGTGAGCCGACACAACAACTGTTAGCTGACCAGC
211  AGGATCGGGCGCTCTTACCGGTCTGTTCACCCGCATATCTGAACGGACGGCTGGAGCCACCCGCAAGCAAT
281  TCATCGACTACTGCGTCAACATGTTGCTCAGCACCCGCCGCCACCTACGCACCCGAGCGGGAGA
351  ATCCGAACACTCCATCCCCAGCCGGGCCGCCACAACTGAGGACGACTGGGGTTCACCCCACGGGGCCACCGG
421  GGCCCGCCGATGCCAGCATCCTGCCCGCTGCTGCAGCTCAACATGCCGCGAAGCCCAAACTTGATGC
                                                                   -35
491  TACCGAGAGACACAGATATATTGACTGCAACCATTAGACACAGATAACTGGAGGCGCCATGTCAGCCAAG
              -10        +1                                         M  S  A  K
561  CTGACCGACCTGCAGCTGCTGCACGAACTTGAACCGGTCGTCGAGAAGTACCTGAACCGGCACCTGAGCA
      L  T  D  L  Q  L  L  H  E  L  E  P  V  V  E  K  Y  L  N  R  H  L  S  M
631  TGCACAAGCCCTGGAACCCGCACGACTACATCCCGTGGTCGGACGGGAAGAACTACTACGCGCTCGGCGG
      H  K  P  W  N  P  H  D  Y  I  P  W  S  D  G  K  N  Y  Y  A  L  G  G
701  GCAGGATTGGGACCCGGACCCCGACCAGAGCAAGCTTTCTGATGTCGCCCAGGTGGCGATGGTGCAGAACCTGGTC
      Q  D  W  D  P  D  Q  S  K  L  S  D  V  A  Q  V  A  M  V  Q  N  L  V
771  ACCGAGGAGACAAACCTGCCTTCGTATCACCGCGAGATCGCGATGAACATGGGACATGGACGGCGCGTGGGGGC  Q
      T  E  D  N  L  P  S  Y  H  R  E  I  A  M  N  M  G  M  D  G  A  W  G  Q
```

```
 841  AGTGGGTCAACCGTTGGACCGCCGAGGAGAATCGGCACGGCATCGCGCTGCGCGACTACCTGGTGGTGAC
       W  V  N  R  W  T  A  E  E  N  R  H  G  I  A  L  R  D  Y  L  V  V  T
 911  CCGATCGGTCGACCCTGTCGAGTTGGAGAAACTTCGCCTCGAGGTAGTCAACCGGGGCTTCAGCCCAGGC
       R  S  V  D  P  V  E  L  E  K  L  R  L  E  V  V  N  R  G  F  S  P  G
 981  CAAAACCACCAGGGCCACTATTCGCGGAGAGCCTCACCGACTCCGTCCTCTATGTCAGTTCCAGGAAC
       Q  N  H  Q  G  H  Y  F  A  E  S  L  T  D  S  V  L  Y  V  S  F  Q  E  L
1051  TGGCAACCCGGATTTCGCCACCGGCAATACCGGCAAGGCATGTAACGACCCCGTCGCCGACCAGCTCATGGC
       A  T  R  I  S  H  R  N  T  G  K  A  C  N  D  P  V  A  D  Q  L  M  A
1121  CAAGATCTCGGCAGACGAGAATCTGCACATGATCTTCTACCGCGACGTCAGCGAGGCCGCGTTCGACCTC
       K  I  S  A  D  E  N  L  H  M  I  F  Y  R  D  V  S  E  A  A  F  D  L
1191  GTGCCCAACCAGGCCATGAAGTCGCTGCACCTGATTTTGAGCCACTTCCAGATGCCCGGCTTCCAAGTAC
       V  P  N  Q  A  M  K  S  L  H  L  I  L  S  H  F  Q  M  P  G  F  Q  V  P
1261  CCGAGTTCCGGCGCAAAGCCGTGGTCATCGCCGTGGTGTCTACGACCCGCGCATCCACCTCGACGA
       E  F  R  R  K  A  V  V  I  A  V  G  G  V  Y  D  P  P  R  I  H  L  D  E
1331  AGTCGTCATGCCGGTACTGAAGAAATGTATCTTCGAGAGGACTTCACCGGCGAGGGGCTAAG
       V  V  M  P  V  L  K  K  W  C  I  F  E  R  E  D  F  T  G  E  G  A  K
1401  CTGCGCGACGAGCTGGCCCTGGTGATCAAGGACCTCGAGCTGGCCTGCGACAAGTTCGAGGTGTCCAAGC
       L  R  D  E  L  A  L  V  I  K  D  L  E  L  A  C  D  K  F  E  V  S  K  Q
1471  AACGCCCAACTCGACCGGGAAGCCGTACGGGCAAGAAGGTCAGCGCACACGAGCTGCATAAAACCGCTGG
       R  Q  L  D  R  E  A  R  T  G  K  K  V  S  A  H  E  L  H  K  T  A  G
1541  CAAACTGGCCGATGAGCCGTCGTTAGCCCGGCGACGATGCAGAGCGCGCAGCCGCGATGAGC
       K  L  A  M  S  R  R  *
```

| Strain or plasmid | Relevant characteristics |
|---|---|
| E. coli DH5α | F/endA1 hsdR17($r_k^- m_k^-$) supE44 thi-1 recA1 gyrA (Nal$^r$) relA1 Δ(lacZYA-argF)U169 deoR (Φ80fdlacΔ(lacZ)M15) |
| E. coli BL21(DE3)pLysS | F- ompT hsdS$_B$($r_B^- m_B^-$); an E. coli B strain) with a λ prophage carrying the T7 RNA polymerase gene. |
| M. smegmatis mc²155 | High transformation mutant of M. smegmatis ATCC607 |
| M. tuberculosis H37Rv | Virulent strain of mycobacterium originally isolated from tuberculosis patient |
| pBluescript KS- | Phagemid derived from pUC19 cloning vector |
| pYUB18 | (Km)$^R$ shuttle vector used for the construction of a M. tuberculosis cosmid library |
| pJEM11 | E.coli-mycobacterium shuttle vector carrying a truncated phoA gene |
| pET14b | pBR322 derivative containing a T7 promoter for expression of target DNAs. |
| pExp421 | pJEM11 vector carrying the 1.1 kb insert from the des-PhoA fusion |
| pBS-des | pBluescript KS- vector carrying the EcoRV 4.5kb insert containing the des gene |
| pET-des | pET14b vector carrying the (JD8-JD9)des PCR amplification product |

FIG. 8

1. Pool of sera from tuberculous cattle
2. Pool of sera from lepromatous leprosy patients
3. Individual sera from *M. bovis*-infected tuberculous patients
4. Individual sera from *M. tuberculosis*-infected tuberculous patients

DESATURASE ANTIGEN OF MYCOBACTERIUM TUBERCULOSIS

This is a division of application Ser. No. 10/368,433, filed Feb. 20, 2003 (now U.S. Pat. No. 7,071,320), which is a division of application Ser. No. 09/230,485, filed Apr. 20, 1999 (now U.S. Pat. No. 6,582,925), which is a 35 U.S.C. §371 filing of PCT/IB97/00923, filed Jul. 25, 1997, and claims priority to Provisional Application No. 60/022,713, filed Jul. 26, 1996. Applicants hereby claim priority to each of those applications under the provisions of 35 U.S.C. §§120, 119, and 365. The entire contents of each of the priority applications is hereby incorporated herein by reference.

BACKGROUND OF THE INVENTION

Tuberculosis and leprosy, caused by the bacilli from the *Mycobacterium tuberculosis* complex and *M. leprae* respectively are the two major mycobacterial diseases. Pathogenic mycobacteria have the ability to survive within host phagocytic cells. From the interactions between the host and the bacteria results the pathology of the tuberculosis infection through the damages the host immune response causes on tissues (Andersen & Brennan, 1994). Alternatively, the protection of the host is also dependent on its interactions with mycobacteria.

Identification of the bacterial antigens involved in these interactions with the immune system is essential for the understanding of the pathogenic mechanisms of mycobacteria and the host immunological response in relation to the evolution of the disease. It is also of great importance for the improvement of the strategies for mycobacterial disease control through vaccination and immunodiagnosis.

Through the years, various strategies have been followed for identifying mycobacterial antigens. Biochemical tools for fractionating and analysing bacterial proteins permitted the isolation of antigenic proteins selected on their capacity to elicit B or T cell responses (Romain et al., 1993; Sorensen et al., 1995). The recent development of molecular genetic methods for mycobacteria (Jacobs et al., 1991; Snapper et al., 1990; Hatful, 1993; Young et al., 1985) allowed the construction of DNA expression libraries of both *M. tuberculosis* and *M. leprae* in the λgt11 vector and their expression in *E. coli* The screening of these recombinant libraries using murine polyclonal or monoclonal antibodies and patient sera led to the identification of numerous antigens (Braibant et al., 1994; Hermans et al., 1995; Thole & van der Zee, 1990). However, most of them turned out to belong to the group of highly conserved heat shock proteins (Thole & van der Zee, 1990; Young et al., 1990).

The observation in animal models that specific protection against tuberculosis was conferred only by administration of live BCG vaccine, suggested that mycobacterial secreted proteins might play a major role in inducing protective immunity. These proteins were shown to induce cell mediated immune responses and protective immunity in guinea pig or mice model of tuberculosis (Pal & Horwitz, 1992; Andersen, 1994; Haslow et al., 1995). Recently, a genetic methodology for the identification of exported proteins based on PhoA gene fusions was adapted to mycobacteria by Lim et al. (1995). It permitted the isolation of *M. tuberculosis* DNA fragments encoding exported proteins. Among them, the already known 19 kDa lipoprotein (Lee et al., 1992) and the ERP protein similar to the *M. leprae* 28 kDa antigen (Berthet et al., 1995).

SUMMARY OF THE INVENTION

We have characterized a new *M. tuberculosis* exported protein named DES identified by using the PhoA gene fusion methodology. The des gene, which seems conserved among mycobacterial species, encodes an antigenic protein highly recognized by human sera from both tuberculosis and leprosy patients but not by sera from tuberculous cattle. The amino acid sequence of the DES protein contains two sets of motifs that are characteristic of the active sites of enzymes from the class II diiron-oxo protein family. Among this family, the DES protein presents significant homologies to soluble stearoyl-ACP desaturases.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

DESCRIPTION OF THE PREFERRED EMBODIMENTS

The invention will be further clarified by the following examples, which are intended to be purely exemplary of the invention.

Bacteria, Media and Growth Conditions

The bacterial strains and plasmids used in this study are listed in FIG. 8 *E. coli* DH5α of BL21 (DE3)pLysS cultures were routinely grown in Luria B medium (Difco) at 37° C. Mycobacterium cultures were grown in Middlebrook 7H9 medium (Difco) supplemented with Tween 0.05%, glycerol (0.2%) and ADC (glucose, 0.2%; BSA fraction V, 0.5%; and NaCl, 0.085%) at 37° C. Antibiotics when required were added at the following concentrations: ampicillin (100 µg/ml), kanamycin (20 µg/ml).

Human and Cattle Sera

Serum specimens from 20 individuals with pulmonary or extra-pulmonary tuberculosis (*M. tuberculosis* infected) were obtained from the Bligny sanatorium (France). 6 sera from *M. bovis* infected human tuberculous patients and 24 sera from BCG-vaccinated patients suffering from other pathologies were respectively obtained from Institut Pasteur, (Madagascar), and the Centre de Biologie Médicale specialisée (CBMS) (Institut Pasteur, Paris). Sera from tuberculous cattle (*M. bovis* infected) were obtained from CNEVA, (Maison Alfort).

Subcloning Procedures

Restriction enzymes and T4 DNA ligase were purchased from Gibco/BRL, Boehringer Mannheim and New England Biolabs. All enzymes were used in accordance with the manufacturer's recommendations. A 1-kb ladder of DNA molecular mass markers was from Gibco/BRL. DNA fragments used in the cloning procedures were gel purified using the Geneclean II kit (BIO 101 Inc., La Jolla, Calif.). Cosmids and plasmids were isolated by alkaline lysis (Sambrook et al., 1989). Bacterial strains were transformed by electroporation using the Gene Pulser unit (Bio-Rad Laboratories, Richmond, Calif.).

BRIEF DESCRIPTION OF THE DRAWINGS

FIG. 2 shows the nucleotide (SEQ ID NO:1) and derived amino acid (SEQ ID NO:2) sequences of the *M. tuberculosis* des gene.

FIG. 3 shows a comparative sequence analysis of class II diiron-oxo proteins and the *M. tuberculosis* Des protein. Shaded residues indicate cluster ligands and probable iron ligands in the *M. tuberculosis* Des protein. Bold unshaded framed letters are probable residues involved in the network of hydrogen bonds to the cluster. Other bold letters indicate conserved residues that are believed to participate in the $O_2$-binding site. Gaps introduced into the sequence of Des are indicated by dots. Accession numbers are as follows ribonucleotide reductases: v01555, Epstein-barr virus; k02672, *E. Coli*. Methane monooxygenase hydroxylases: M58499, *Methylococcus capsulatus*; X55394, mmoX *Methylosinus trichosporium*; M60276, *Pseudomonas* sp. strain CF 600 phenol hydroxylase dmpN polypeptide; M65106, *Pseudomonas mendocina* KR1. Stearoyl-ACP desaturases: M59857, *Ricinus communis*; M59858, cucumber; M61109, safflower; X62898, spinach; X60978, *Brassica*; M91238, potato; X70962, linseed; M93115, coriander Delta-4 desaturase.

FIG. 4 is a Southern blot analysis of the distribution of the des gene in other mycobacterial species. DNA from various mycobacterial strains were Pstl-digested, electrophoresed, transferred onto a nylon membrane by Southern blotting, and hybridized using probe B, which is shown in FIG. 1.

FIG. 5 shows an SDS-PAGE gel of soluble and insoluble extracts from *E. coli* expressing the DES protein on plasmid pETdes (1-1718).

FIG. 6 shows the results of ELISAs of the sensitivity of the antibody response to the DES antigen of human tuberculous and non-tuberculous patients.

FIG. 7 shows the nucleotide sequence of the first 1600 nucleotides of the *Mycoplasma tuberculosis* des gene (SEQ ID NO: 1) and derived amino acid (SEQ ID NO: 2) sequence of the *Mycoplasma tuberculosis* des gene. The underlined sequences correspond to the −35 and −10 boxes of the promoter and a Shine Dalgarno sequence that corresponds to the putative ribosomal attachment site, respectively. The adenosine labelled "+1" corresponds to the transcription initiation site.

FIG. 8 is a table of the bacterial strains and plasmids used in this application.

FIG. 9 is a Western blot showing the recognition of the purified DES protein by antibodies from *M. bovis* and *M. tuberculosis*-infected humans and cattle.

Southern Blot Analysis and Colony Hybridization.

DNA fragments for radiolabeling were separated on 0.7% agarose gels (Gibco BRL) in a Tris-borate-EDTA buffer system (Sambrook et al., 1989) and isolated from the gel by using Geneclean II (BIO 101). Radiolabeling was carried out with the random primed labeling kit Megaprime (Amersham) with 5 μCi of (α-$^{32}$P)dCTP, and nonincorporated label was removed by passing through a Nick Column (Pharmacia). Southern blotting was carried out in 0.4 M NaOH with nylon membranes (Hybond-N+, Amersham) according to the Southern technique (Southern, 1975), prehybridization and hybridization was carried out as recommended by the manufacturer using RHB buffer (Amersham). Washing at 65° C. was as follows: two washes with 2×SSPE (150 mM NaCl, 8.8 mM $NaH_2PO_4$, 1 mM EDTA pH 7.4)-SDS 0.1% of 15 minutes each, one wash with 1×SSPE-SDS 0.1% for 10 minutes, two washes with 0.7×SSPE-SDS 0.1% of 15 minutes each. Autoradiographs were prepared by exposure with X-ray film (Kodak X-Omat AR) at −80° C. overnight. Colony hybridization was carried out using nylon membrane discs (Hybond-N+ 0.45 μm, Amersham). *E. coli* colonies adsorbed on the membranes were lysed in a (0.5 M NaOH, 1.5 M NaCl) solution, before being placed for one minute in a micro-wave oven to fix the DNA. Hybridization and washings were as described for the Southern blotting analysis.

DNA Sequencing and Analysis

Sequences of double-stranded plasmid DNA were determined by the dideoxy-chain termination method (Sanger et al., 1977) using the Taq Dye Deoxy Terminator Cycle sequencing Kit (Applied Biosystems), on a GeneAmp PCR System 9600 (Perkin Elmer), and run on a DNA Analysis System-Model 373 stretch (Applied Biosystems). The sequence was assembled and processed using DNA strider™ (CEA, France) and the University of Wisconsin Genetics Computer Group (UWGCG) packages. The BLAST algorithm (Altschul et al., 1990) was used to search protein data bases for similarity.

Expression and Purification of the DES Protein in *E. coli*

A 1043 bp NdeI-BamHI fragment of the des gene was amplified by PCR using nucleotides JD8 (5'-CGGCATATGTCAGCCAAGCTGACCGACCTGCAG-3') (SEQ ID NO: 3) and JD9 (5'-CGGATCCCGCGCTCGCCGCTCTGCATCGTCG-3')(SEQ ID NO: 4), and cloned into the NdeI-BamHI sites of pET14b (Novagen) to generate pET-des. PCR amplifications were carried out in a DNA thermal Cycler (Perkin Elmer), using Taq polymerase (Cetus) according to the manufacturer's recommendations. PCR consisted of one cycle of denaturation (95° C., 6 min) followed by 25 cycles of amplification consisting of denaturation (95° C., 1 min), annealing (57° C., 1 min), and primer extension (72° C., 1 min). In the pET-des vector, the expression of the des gene is under control of the T7 bacteriophage promoter and the DES antigen is expressed as a fusion protein containing six histidine residues. Expression of the des gene was induced by addition of 0.4 mM IPTG in the culture medium. The DES protein was purified by using a nickel-chelate affinity resin according to the recommendations of the supplier (Qiagen, Chatsworth, Calif.). Linked to the localization of the DES protein in cytoplasmic inclusion bodies, the purification was carried out under denaturating conditions in guanidine hydrochloride buffers. The protein was eluted in buffer A (6 M guanidine hydrochloride, 0.1 M $NaH_2PO_4$, 0.01 M Tris, pH 8) containing 100 mM EDTA. The purified protein was kept and used in buffer A, as all attempts to solubilize it in other buffers were unsuccessful.

SDS-PAGE and Immunoblotting

Sodium dodecyl sulfate-polyacrylamide gel electrophoresis (SDS-PAGE) was carried out as described by Laemmli (1970). For Western blotting experiments (immunoblotting), approximately 10 μg of DES purified protein were run on a SDS-polyacrylamide gel and transferred onto nitrocellulose membranes (Hybond C extra, Amersham) using a Bio-Rad mini transblot apparatus according to the recommendations of the manufacturer (Bio-Rad Laboratories, Richmond, Calif.). Transfer yield was visualized by transient staining with Ponceau Rouge. The membrane were incubated with human patient or cattle sera diluted 1/200$^{e}$ at 37° C. for 1 hour and with a goat anti-human (Promega) or rabbit anti-cattle (Biosys)IgG alkaline phosphatase-conjugated secondary antibody diluted 1/2500$^{e}$ for 30 minutes at 37° C. The color reaction was performed by addition of 5-bromo-4-chloro-3-indolylphosphate (0.165 mg/ml) and toluidinum nitroblue tetrazolium (0.33 mg/ml) as substrates.

ELISA

The human or cattle sera were tested for antibodies against DES by enzyme-linked immunosorbent assay (ELISA). The 96-well micro-titer trays (Nunc) were coated with 0.1 µg (per well) of purified DES protein in guanidine hydrochloride buffer A (6 M guanidine hydrochloride, 0.1 M $NaH_2PO_4$, 0.01 M Tris, pH 8) (1 h at 37° C. and 16 h at 4° C.). After three washes, wells were saturated with bovine serum albumin 3% in phosphate buffered saline (PBS) for 30 min at room temperature. After three washes, sera diluted from $1/50^e$ to $1/3200^e$ in buffer (PBS, 0.1% Tween 20, 1% bovine serum albumin) were added to the wells for 2 h at 37° C. After three washes, the wells were treated with goat anti-human IgG-alkaline phosphatase conjugate (Promega) diluted $1/4000^e$ for 1 h at 37° C. Then, 4 mg of p-nitrophenylphosphate per ml were added as substrate. After 20 min of incubation at 37° C., the plates were read photometrically at an optical density of 405 nm in micro-ELISA Autoreader (Dynatech, Marnes la Coquette, France).

Statistics

Antibody response of the different sera tested were compared by using the Student t test. $P \geq 0.05$ was considered nonsignificant.

Nucleotide Sequence and Accession Number

The nucleotide sequences of des has been deposited in the Genome Sequence Data Base (GSDB) under the accession number U49839.

Cloning of the Des Gene

The construction of a library of fusions of *M. tuberculosis* genomic DNA to the phoA gene and its expression in *M. smegmatis*, described by Lim et al. (1995), led to the isolation of several PhoA$^+$ clones. pExp421 is the plasmid harboured by one of the PhoA$^+$ clones selected from this library. Detection of enzymatically active alkaline phosphatase indicated that the pExp421 insert contains functional expression and exportation signals. Restriction analysis showed that pExp421 carries a 1.1 kb insert. Partial determination of its sequence identified a 577 bp ORF, named des, fused in frame to the phoA gene and presenting two motifs, of 9 and 14 amino acids, conserved with soluble stearoyl-acyl-carrier protein desaturases (Lim et al., 1995).

Figure 1:
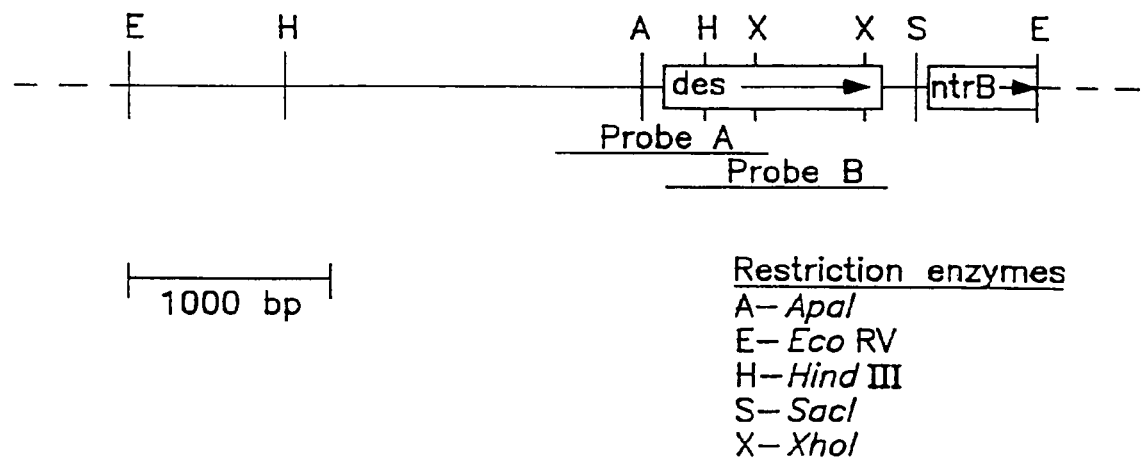
FIG. 1 is a restriction map of the 4.5 kb EcoRV fragment encoding the M. tuberculosis des gene.

To isolate the full-lengh des gene, the *M. tuberculosis* H37Rv pYUB18 genomic cosmid library (Jacobs et al., 1991), was screened by colony hydridization with the 1.1 kb probe (probe A, see FIG. 1). Two hybridizing cosmids named $C_3$ and $C_4$ were selected for further isolation of the gene. $C_3$ and $C_4$ were cut with several restriction enzymes and subjected to Southern blot analysis using the 1.1 kb fragment as a probe.

The EcoRV restriction profile revealed a single hybridizing fragment of 4.5 kb which was subcloned into pBluescript KS$^-$ (Stratagène) to give plasmid pBS-des.

Characterization of the Des Gene

The DNA sequence of the full des ORF was determined (FIG. 2). The des gene was shown to cover a 1017 bp region, encoding a 339 amino acid protein with a calculated molecular mass of 37 kDa. The ORF starts with a potential ATG start codon at position 549, and ends with a TAG stop codon at position 1565. There is a potential Shine-Dalgarno motif (GGAGG) at position −8 upstream of the ATG. The G+C content of the ORF (62%) is consistent with the global GC content observed in mycobacterial genome. The nucleotide and deduced amino acid sequences of the des gene were compared to sequences in databases. They showed very high homologies to the *M. leprae* aadX gene located on cosmid B2266, deposited in GenBank as part of the *M. leprae* genome sequencing project (GenBank accession number n° U15182). Within the coding region, the DNA sequences were 79% identical while the encoded proteins were 80% identical (88% including conserved residues). The des gene also scored significantly against soluble stearoyl-ACP desaturases: 44% identity at the nucleotide level, 30% identity (51% including conserved residues) at the amino acid level, to the *Oryza sativa* stearoyl-ACP desaturase (accession n° D38753).

Although the detection of a phoA enzymatical activity in the *M. smegmatis* clone harbouring the pExp421 suggests the DES protein is exported, no structural similarities were found between the DES protein N terminal amino acids and signal sequences of bacterial exported proteins (Izard & Kendall, 1994).

Like in *M. leprae* genome, a second ORF presenting high homologies to the *M. leprae* putative NtrB gene (cosmid B2266), is located downstream of the des gene in *M. tuberculosis* FIG. 2. Interestingly, the two ORF, des and "NtrB", are separated in *M. tuberculosis* by two direct repeats of 66 nucleotides overlapping on 9 nucleotides (FIG. 2). Although *M. leprae* and *M. tuberculosis* seem to share the same genomic organization in this part of the chromosome, these repeats are absent from the *M. leprae* genome.

The Des Protein Presents the Conserved Amino Acid Motifs of the Class II Diiron-Oxo Proteins Further analysis of the amino-acid sequence of the DES protein revealed the presence of conserved motifs found only in class II diiron-oxo proteins (Fox et al., 1994) (FIG. 3). These proteins are oxo-bridged diiron clusters (Fe—O—Fe) containing proteins. They possess in their secondary structure 4 alpha helices involved in the protein-derived cluster ligands. As revealed by X-ray structure studies, in these proteins, the diiron axis is oriented parallel to the long axis of the four helix bundle with ligands arising from four noncontiguous helices, B, C, E and F. *M. tuberculosis* DES protein appears to have the same active site residues as the class 11 diiron-oxo enzymes. This includes Glu and His residues ($E_{107}$ and $H_{110}$ in helix C, $E_{167}$ in helix E and $E_{197}$ and $H_{200}$ in helix F) that are ligands to the iron atoms, Asp, Glu and Arg residues ($E_{106}$ and $R_{109}$ in helix C, $D_{196}$ in helix F) that are involved in a hydrogen-bonding network to the cluster and, Ile and Thr residues that may be part of the $O_2$-binding site ($T_{170}$ in helix E, $I_{193}$ in helix F). Thus, the *M. tuberculosis* DES protein contains in its primary sequence two conserved D/E(ENXH) motifs separated by 85 amino acids.

The class II diiron-oxo protein family contains up to date ribonucleotide reductases, hydrocarbon hydroxylases (methane monooxygenase, toluene-4-monooxygenase and phenol hydroxylase) and soluble-ACP desaturases. On the overall sequence alignment the DES protein presents higher homology to soluble stearoyl-ACP desaturases than to ribonucleotide reductases or bacterial hydroxylases. The percentage identity at the amino acid level of the DES protein was said to be 30% with the Oryza sativa stearoyl-ACP desaturase, whereas it is only 17% with the *Methylococcus capsulatus* methane monooxygenase (accession n° M58499), 17.5% with the *Pseudomonas* sp CF 600 phenol hydroxylase (accession n° M60276) and 17.7% with the Epstein Barr ribonucleotide reductase (accession n° V01555). Homologies to the soluble Δ9 desaturases mostly concern the amino acids located within the active site in helices C, E and F (FIG. 3).

Distribution of the Des Gene in Other Mycobacterial Species

Figure 4:
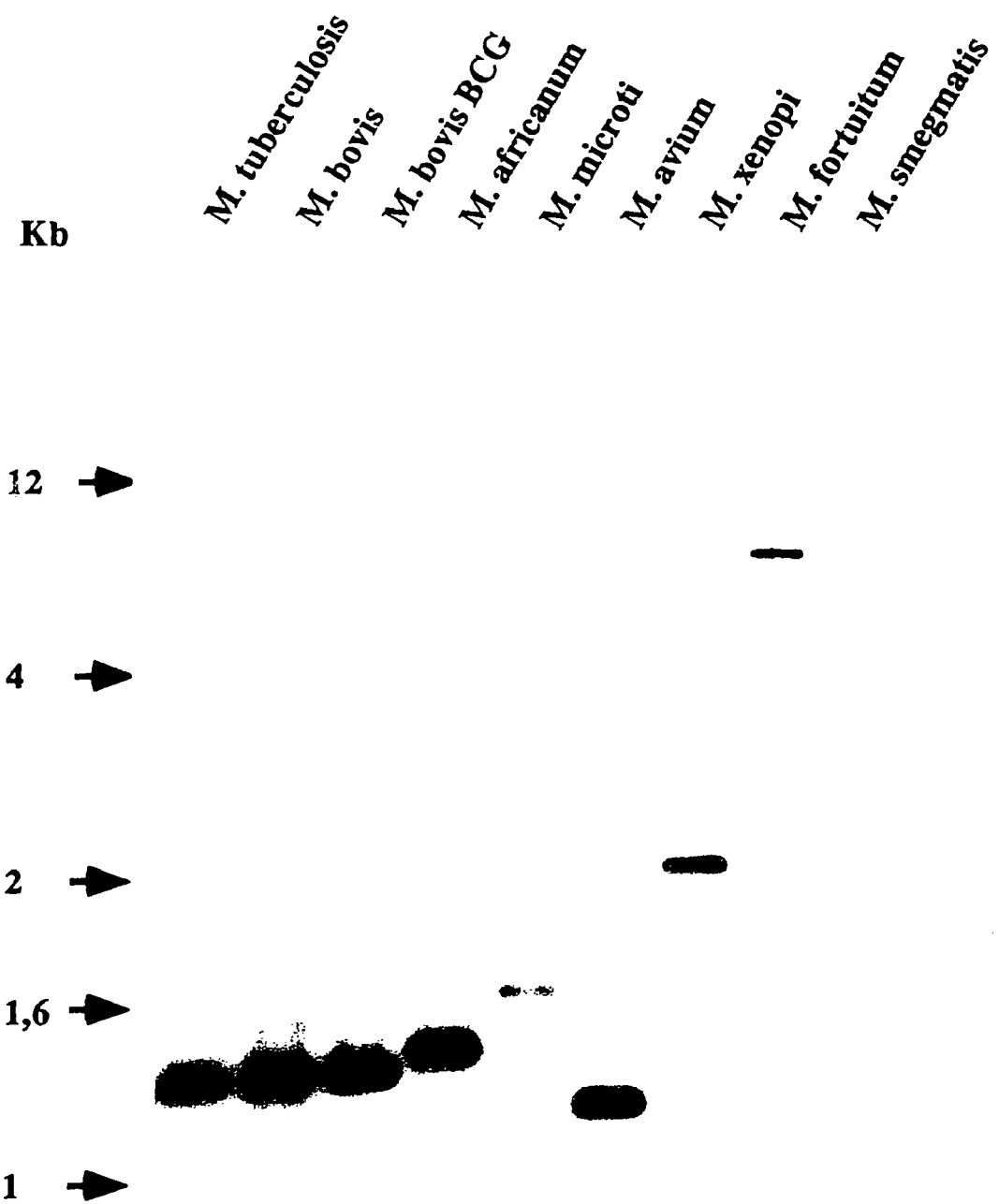

The presence of the des gene in PstI-digested chromosomal DNA from various mycobacterial strains was analyzed by Southern blotting (FIG. 4). The probe used (probe B) is a PCR amplification product corresponding to nucleotides 572 to 1589 (see FIG. 1). The probe hybridized on all mycobacterial genomic DNA tested. Strong signals were detected in *M. tuberculosis*, *M. bovis*, *M. bovis* BCG, *M. Africanum* and *M. avium*. Weaker signals were visible in *M. microti*, *M. xenopi*, *M. fortuitum* and *M. smegmatis*. Thus, the des gene seems to be present in single copy at least in the slow growing *M. tuberculosis*, *M. bovis*, *M. bovis* BCG, *M. Africanum*, *M. avium* and *M. xenopi* as well as in the fast growing *M. smegmatis*.

Expression of the Des Gene in *E. coli*

Figure 5:
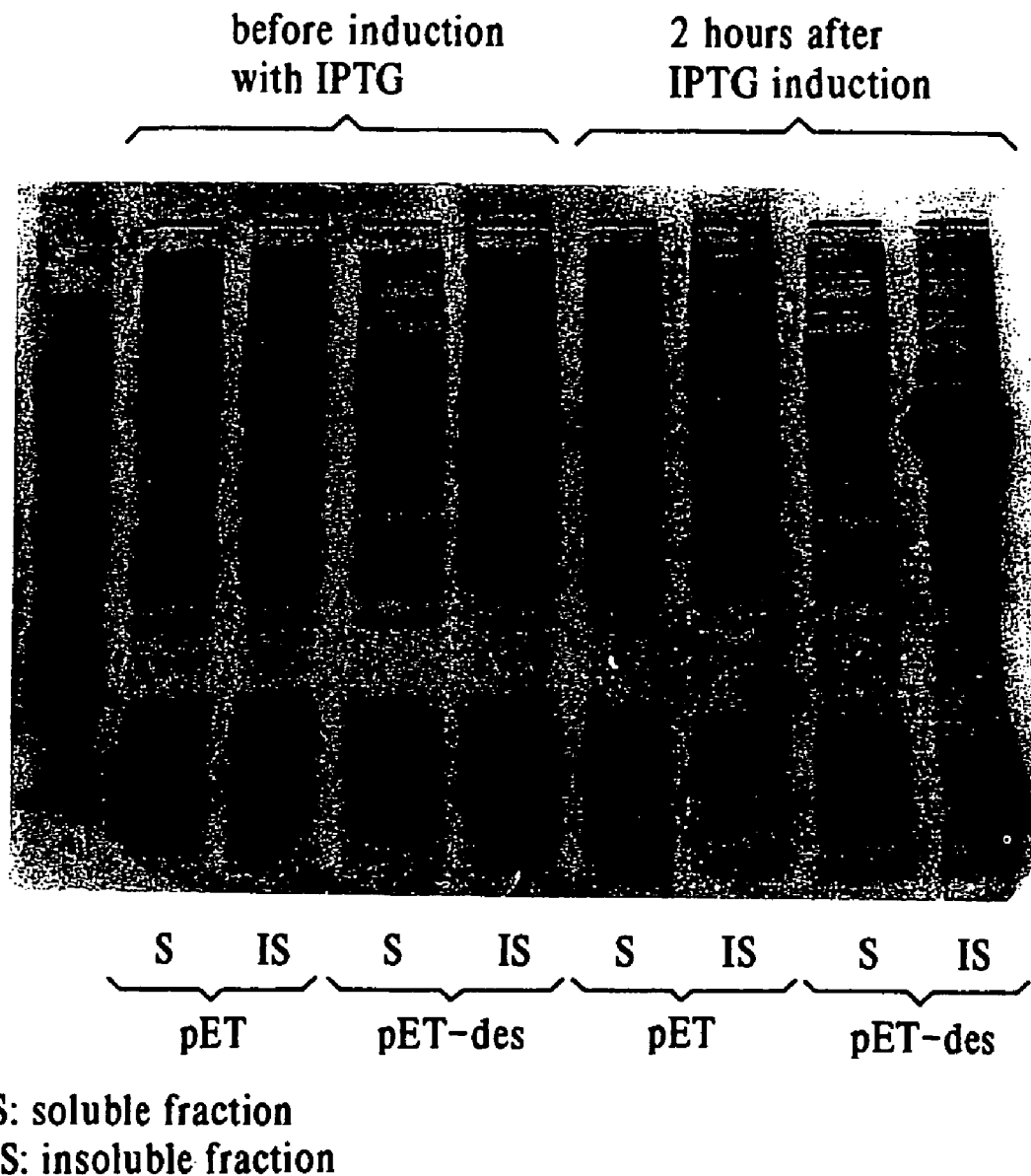

In order to overexpress the DES protein, the des gene was subcloned into the bacteriophage T7 promoter-based expression vector pET14b (Novagen). A PCR amplification product of the des gene (see material and methods) was cloned into the NdeI-BamHI sites of the vector, leading to plasmid pET-des. Upon IPTG induction of *E. coli* BL21 DE3 pLysS cells harbouring the plasmid pET-des, a protein of about 40 kDa was overproduced. The size of the overproduced protein is in agreement with the molecular mass calculated from the deduced polypeptide. As shown in FIG. 5, the great majority of the overproduced DES protein is present in the insoluble matter of *E. coli* cells. This probably results from the precipitation of the over-concentrated protein in *E. coli* cytoplasm thus forming inclusion bodies. To be able to dissolve the protein, the purification was carried out using a nickel chelate affinity resin under denaturing conditions in guanidine hydrochloride buffers. Among all the conditions tested (pH, detergents . . . ), the only condition in which the protein could be eluted without precipitating in the column and remain soluble, was in a buffer containing 6 M guanidine hydrochloride.

Figure 9:
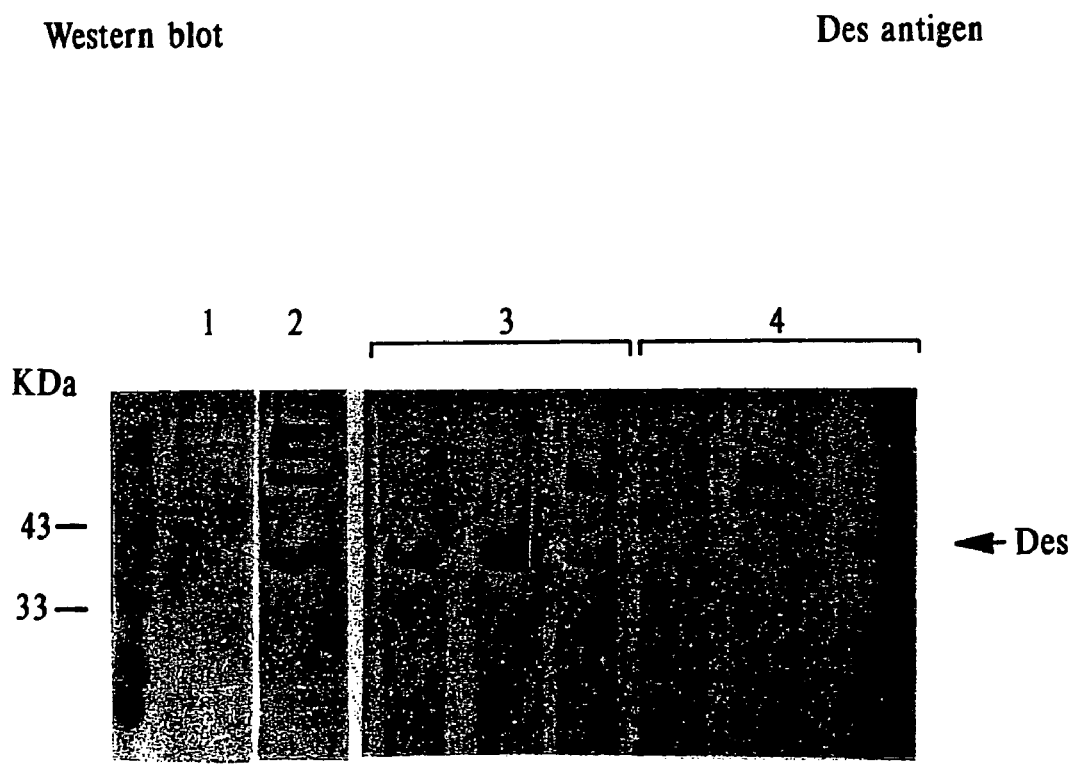

Immunogenicity of the DES Protein After Infection 20 serum samples from *M. tuberculosis* infected human patients (4 with extra-pulmonary tuberculosis, 15 with pulmonary tuberculosis and 1 with both forms of the disease), 6 sera from *M. bovis* infected human patients and 4 sera from *M. bovis* infected cattle were tested either pooled or taken individually in immunoblot experiments to determine the frequency of recognition of the purified DES protein by antibodies from infected humans or cattle. 20 out of the 20 sera from the *M. tuberculosis* infected human patients and 6 out of the 6 sera from the *M. bovis* infected human patients recognized the recombinant antigen as shown by the reaction with the 37 kDa band (FIG. 9). Furthermore, a pool of sera from human lepromatous leprosy patients also reacted against the DES antigen.

In contrast, the pool of serum specimens from *M. bovis* infected cattle did not recognize the DES protein. These results indicate that the DES protein is highly immunogenic in tuberculosis human patients. Both pulmonary and extra-pulmonary tuberculosis patients recognize the antigen.

Magnitude of Human Patients Antibody Response

Figure 6:
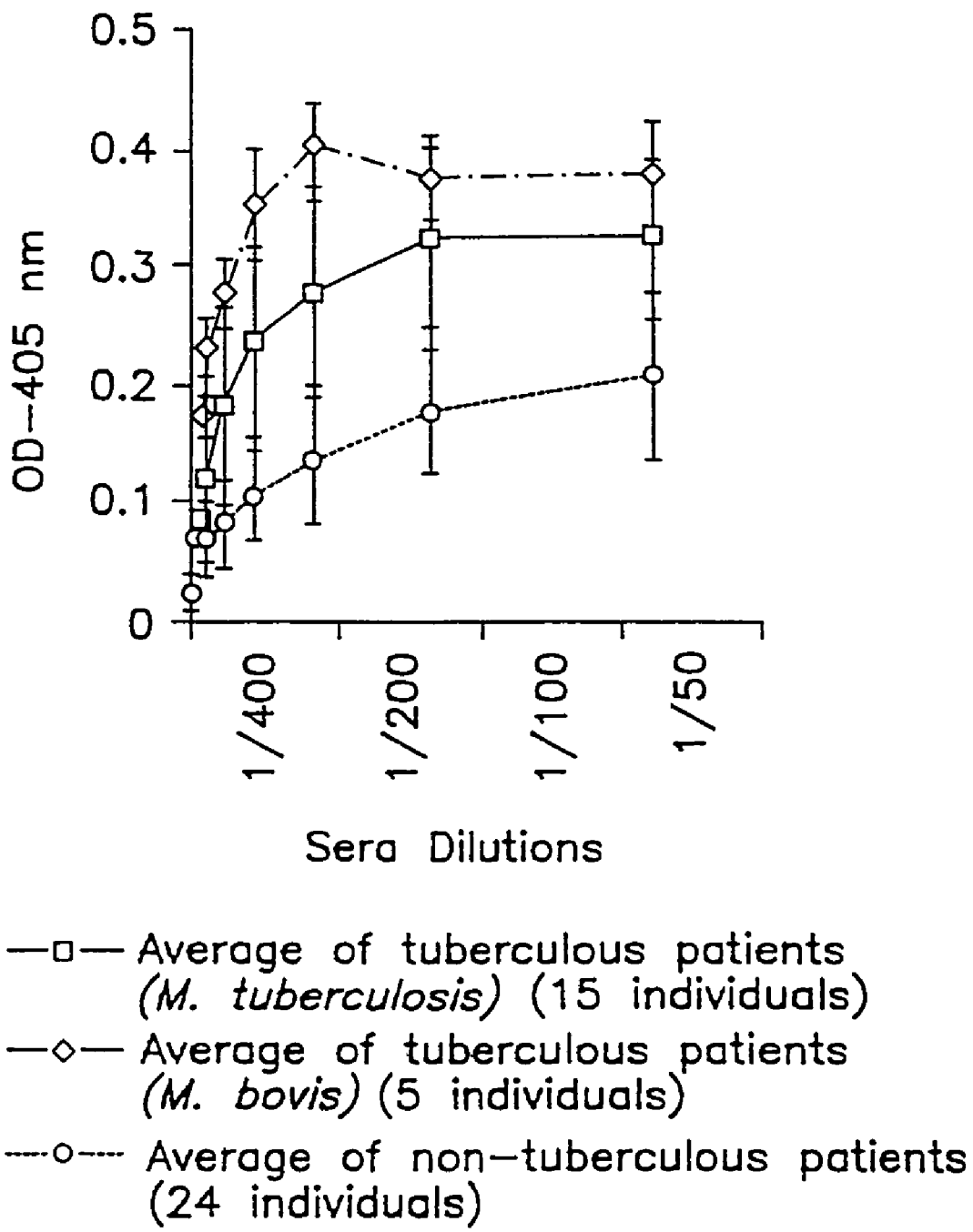

An enzyme-linked immunosorbent assay (ELISA) was used to compare the sensitivity of the different serum samples from 20 tuberculosis patients (15 infected by *M. tuberculosis* and 5 infected by *M. bovis*) to the DES antigen. This technique was also carried out to compare the sensitivity of the antibody response to DES of the 20 tuberculosis patients to the one of 24 patients (BCG-vaccinated) suffering from other pathologies. As shown on FIG. 6, patients suffering from other pathologies than tuberculosis, react at a low level to the DES antigen (average $OD_{405}$=0.17 for a serum dilution $1/100^e$). The average antibody response from the tuberculosis patients infected by *M. tuberculosis* or *M. bovis* against the same antigen is much more sensitive ($OD_{405}$=0.32 and $OD_{405}$=0.36 respectively, for a serum dilution $1/100^e$). This difference in the sensitivity of the immunological response is statistically highly significant at every dilution from $1/50^e$ to $1/3200^e$ as shown by a Student $t_{95}$ test ($t_{95}$=5.18, 6.57, 6.16, 5.79, 4.43, 2.53 and 1.95, at sera dilutions $1/50^e$, $1/100^e$, $1/200^e$, $1/400^e$, $1/800^e$, $1/1600^e$ and $1/3200^e$, respectively).

No differences in the sensitivity of the antibody response was noticed between patients suffering from pulmonary or extra-pulmonary tuberculosis.

The PhoA gene fusion methodology permitted the identification of a new *M. tuberculosis* exported antigenic protein.

This 37 kDa protein contains conserved amino acid residues which are characteristic of class 11 diiron-oxo-proteins. Proteins from that family are all enzymes that require iron for activity. They include ribonucleotide reductases, hydrocarbon hydroxylases and stearoyl-ACP desaturases. The *M. tuberculosis* DES protein only presents significant homologies to plant stearoyl-ACP desaturases (44% identity at the nucleotide level, and 30% identity at the amino-acid level) which are also exported enzymes as they are translocated across the chloroplastic membranes (Keegstra & Olsen, 1989). This result suggests that the DES protein could be involved in the mycobacterial fatty acid biosynthesis. Furthermore, the localization of the protein outside the cytoplasm would be consistent with its role in the lipid metabolism, since lipids represent 60% of the cell wall constituents and that part of the biosynthesis of the voluminous mycolic acids containing 60 to 90 carbon atoms occurs outside the cytoplasm. Among all the different steps of the lipid metabolism, desaturation reactions are of special interest, first because they very often take place at early steps of lipid biosynthesis and secondly because, through the control they have on the unsaturation rate of membranes, they contribute to the adaptation of mycobacteria to their environment (Wheeler & Ratledge, 1994). An enzyme system involving a stearoyl-Coenzyme A desaturase (analog of the plant stearoyl-ACP-desaturases), catalyzing oxydative desaturation of the CoA derivatives of stearic and palmitic acid to the corresponding Δ9 monounsaturated fatty acids has been biochemically characterized in *Mycobacterium phlei* (Fulco & Bloch, 1962; Fulco & Bloch, 1964; Kashiwabara & al., 1975; Kashiwabara & Sato, 1973). This system was shown to be firmly bound to a membranous structure (Fulco & Bloch, 1964). Thus, *M. tuberculosis* stearoyl-Coenzyme A desaturase (Δ9 desaturase) is expected to be an exported protein. Sonicated extracts of *E. coli* expressing the DES protein were assayed for Δ9 desaturating activity according to the method described by Legrand and Besadoun (1991), using (stearoyl-CoA) $^{14}$C as a substrate. However, no Δ9 desaturating activity could be detected. This result is probably linked to the fact desaturation systems are multi-enzyme complexes involving electron transport chains and numerous cofactors, often difficult to render functional in vitro. *E. coli* and mycobacteria being very different from a lipid metabolism point of view, the *M. tuberculosis* recombinant Δ9 desaturase might not dispose in *E. coli* of all the cofactors and associated enzymes required for activity or might not interact properly with them. Moreover, not all cofactors involved in the Δ9 desaturation process of mycobacteria are known, and they might be missing in the incubation medium.

However, if the DES protein encodes a Δ9 desaturase, an amazing point concerns its primary sequence. Indeed, all animal, fungal and the only two bacterial Δ9 desaturases sequenced to date (Sakamoto et al., 1994) are integral membrane proteins which have been classified into a third class of diiron-oxo proteins on the basis of their primary sequences involving histidine conserved residues (Shanklin et al., 1994). The plant soluble Δ9 desaturases are the only desaturases to possess the type of primary sequence of class II diiron-oxo proteins (Shanklin & Somerville, 1991). No bacteria have yet been found which have a plant type Δ9 desaturase.

As shown by immunoblotting and ELISA experiments, the DES protein is a highly immunogenic antigen which elicits B cell response in 100% of the tuberculosis *M. bovis* or *M. tuberculosis*-infected human patients tested, independently of the form of the disease (extrapulmonary or pulmonary). It also elicits an antibody response in lepromatous leprosy patients. Interestingly, although more sera would need to be tested, tuberculous cattle do not seem to recognize the DES antigen. Furthermore, the ELISA experiments showed that it is possible to distinguish tuberculosis patients from patients suffering from other pathologies on the basis of the sensitivity of their antibody response to the DES antigen. The DES antigen is therefore a good candidate to be used for serodiagnosis of tuberculosis in human patients. The reason why the non-tuberculous patients tested recognize at a low level the DES protein could be due to the fact they are all BCG-vaccinated individuals (BCG expressing the protein), or to a cross-reactivity of their antibody response with other bacterial antigens. It would now be interesting to know whether the DES antigen possesses, in addition to its B cell epitopes, T cell epitopes which are the only protective ones in the host immunological response against pathogenic mycobacteria. If the DES protein is also a good stimulator of the T cell response in a majority of tuberculosis patients, it could be used either individually or as part of a "cocktail" of antigens in the design of a subunit vaccine against tuberculosis.

The references cited herein are listed on the following pages and are expressly incorporated by reference.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

1. Altschul, S. F., W. Gish, W. Miller, E. M. Myers, and D. J. Lipman, 1990. Basic local alignment search tool. Journal of Molecular Biology. 215:403-410.
2. Andersen, A. B., and P. Brennan, 1994. Proteins and antigens of *Mycobacterium tuberculosis*, p. 307-332. In B. R. Bloom (ed.), Tuberculosis: Pathogenesis, Protection, and Control. ASM, Washington, D.C.
3. Andersen, P. 1994. Effective vaccination of mice against *Mycobacterium tuberculosis* infection with a soluble mixture of secreted mycobacterial proteins. Infect. Immun. 62:2536-2544.
4. Berthet, F. X., J. Rauzier, E. M. Lim, W. Philipp, B. Gicquel, and D. Portnoï, 1995. Characterization of the *M. tuberculosis* erp gene encoding a potential cell surface protein with repetitive structures. Microbiology, 141: 2123-2130.
5. Braibant, M., L. D. Wit, P. Peirs, M. Kalai, J. Ooms, A. Drowart, K. Huygen, and J. Content, 1994. Structure of the Mycobacterium tuberculosis antigen 88, a protein related to the *Escherichia coli* PstA periplasmic phosphate permease subunit, Infection and Immunity, 62:849-854.
6. Fox, B. G., J. Shanklin, J. Ali, T. M. Loerh, and J. Sanders-Loerb, 1994. Resonance Raman evidence for an Fe—O—Fe center in stearoyl-ACP desaturase. Primary sequence identity with other diiron-oxo proteins. Biochemistry 33:12776-12786.
7. Fulco, A. J., and K. Bloch, 1962. Cofactor requirements for fatty acid desaturation in *Mycobacterium phlei*. Biochim. Biophys. Acta. 63:545-546.
8. Fulco, A. J., and K. Bloch, 1964. Cofactor requirements for the formation of Δ9 unsatured fatty acids in *Mycobacterium phlei*. The Journal of Biological Chemistry. 239:993-997.
9. Haslov, K., A. Andersen, S. Nagai, A. Gottschau, T. Sorensen, and P. Andersen, 1995. Guinea pig cellular immune responses to proteins secreted by *Mycobacterium tuberculosis*. Infection and Immunity, 63:804-810.
10. Haffull, G. F. 1993. Genetic transformation of mycobacteria. Trends in microbiology, 1:310-314.
11. Hermans, P. W. M., F. Abebe, V. I. O. Kuteyi, A. H. J. Kolk, J. E. R. Thole, and M. Harboe, 1995. Molecular and immunological characterization of the highly conserved antigen 84 from *Mycobacterium tuberculosis* and *Mycobacterium leprae*. Infection and Immunity, 63:954-960.
12. Izard, J. W., and D. A. Kendall, 1994. Signal peptides: exquisitely designed transport promoters, Molecular Microbiology, 13:765-773.
13. Jacobs, W. R., G. V. Kalpana, J. D. Cirillo, L. Pascopella, S. B. Snapper, R. A. Udani, W. Jones, R. G. Barletta, and B. R. Bloom, 1991. Genetic systems for mycobacteria. Methods enzymol. 204:537-555.
14. Kashiwabara, Y., H. Nakagawa, G. Matsuki, and R. Sato, 1975. Effect of metal ions in the culture medium on the stearoyl-Coenzyme A desaturase activity of Mycobacterium phlei. J. Biochem. 78:803-810.
15. Kashiwabara, Y., and R. Sato, 1973. Electron transfer mechanism involved in stearoyl-coenzyme A desaturation by particulate fraction of *Mycobacterium phlei*. J. Biochem. 74:405-413.
16. Keegstra, K., and L. J. Olsen, 1989. Chloroplastic precursors and their transport across the envelope membranes. Ann. Rev. Plant Physiol. Plant Mol. Biol. 40:471-501.
17. Laemmli, U. K. 1970. Cleavage of structural proteins during the assembly of the head of bacteriophage T4. Nature (London). 227:680-685.
18. Lee, B. Y., S. A. Hefta, and P. J. Brennan, 1992. Characterization of the major membrane protein of virulent *Mycobacterium tuberculosis*. Infection and Immunity. 60:2066-2074.
19. Legrand, P., and A. Bensadoun, 1991. Stearyl-CoA desaturase activity in cultured rat hepatocytes. Biochimica et Biophysica Acta. 1086:89-94.
20. Lim, E. M., J. Rauzier, J. Timm, G. Torrea, A. Murray, B. Gicquel, and D. Portnoï, 1995. Identification of Mycobacterium tuberculosis DNA sequences encoding exported proteins by using phoA gene fusions. Journal of Bacteriology. 177:59-65.
21. Pal, P. G., and M. A. Horwitz, 1992. Immunization with extracellular proteins of *Mycobacterium tuberculosis* induces cell-mediated immune responses and substantial protective immunity in a guinea pig model of pulmonary tuberculosis. Infection and Immunity. 60:4781-4792.
22. Romain, F., A. Laqueyrerie, P. Militzer, P. Pescher, P. Chavarot, M. Lagranderie, G. Auregan, M. Gheorghiu, and G. Marchal, 1993. Identification of a *Mycobacterium bovis* BCG 45/47-kilodalton antigen complex, an immunodominant target for antibody response after immunization with living bacteria. Infection and immunity 61:742-750.

23. Sakamoto, T., H. Wada, I. Nishida, M. Ohmori, and N. Murata, 1994. Δ9 acyl lipid desaturases of cyanobacteria. J. Biol. Chem. 269:25576-25580.
24. Sambrook, J., E. F. Fritsch, and T. Maniatis, 1989. Molecular cloning—A laboratory manual. Cold Spring Harbor Laboratory Press. Cold Spring Harbor, N.Y.
25. Sanger, F., S. Nicklen, and A. R. Coulson. 1977. DNA sequencing with chain terminating inhibitors. Proc. Natl. Acad. Sci. USA, 74:5463-5467.
26. Shanklin, J., and C. Somerville, 1991. Stearoyl-acyl-carrier-protein desaturase from higher plants is structurally unrelated to the animal and fungal homologs. Proceeding of the National Academy of Science of the United States of America. 88:2510-2514.
27. Shanklin, J., E. Whittle, and B. G. Fox, 1994. Eight histidine residues are catalytically essential in a membrane-associated iron enzyme, stearoyl-CoA desaturase, and are conserved in alkane hydroxylase and xylene monooxygenase. Biochemistry. 33:12787-12794.
28. Snapper, S. B., B. R. Bloom, and J. W. R. Jacobs, 1990. Molecular genetic approaches to mycobacterial investigation, p. 199-218. In J. McFadden (ed.), Molecular Biology of the Mycobacteria. Surrey University Press, London.
29. Sorensen, A. L., S. Nagai, G. Houen, P. Andersen, and A. B. Andersen, 1995. Purification and characterization of a low-molecular-mass T-cell antigen secreted by *Mycobacterium tuberculosis*. Infection and Immunity 63:1710-1717.
30. Southern, E. M. 1975. Detection of specific sequences among DNA fragments separated by gel electrophoresis. J. Mol. Biol. 98:503-517.
31. Studier, W., A. H. Rosenberg, J. J. Dunn, and J. W. Dubendorff 1990. Use of T7 RNA polymerase to direct expression of cloned genes. Methods in Enzymology 185:60-89.
32. Thole, J. E. R., and R. v. d. Zee 1990. The 65 kD antigen: molecular studies on a ubiquitous antigen, p. 37-66. In J. McFadden (ed.). Molecular Biology of the mycobacteria. Surrey University Press, London.
33. Wheeler, P. R., and C. Ratledge. 1994. Metabolism of *Mycobacterium tuberculosis*, p. 353-385. In B. R. Bloom (ed.). Tuberculosis: Pathogenesis, Protection, and Control, ASM. Washington, D.C.
34. Young, D., T. Garbe, R. Lathigra and C. Abou-Zeid, 1990. Protein antigens: structure, function and regulation, p. 1-35. In J. McFadden (ed.), Molecular biology of mycobacteria. Surrey University Press, London.
35. Young, R. A., B. R. Bloom, C. M. Grossinsky, J. Ivany, D. Thomas, and R. W. Davis, 1985. Dissection of the Mycobacterium tuberculosis antigens using recombinant DNA. Proc. Natl. Acad. Sci. USA 82:2583-2587.

The invention claimed is:

1. A purified antibody that binds to the DES protein of *Mycobacterium tuberculosis* (SEQ ID NO: 2).

2. The antibody according to claim 1, wherein the antibody is a polyclonal antibody.

3. The antibody according to claim 1, wherein the antibody is a monoclonal antibody.

4. A human antibody purified from serum of *Mycobacterium tuberculosis* or *Mycobacterium bovis* infected human patients, wherein said human antibody binds to the purified DES protein of *Mycobacterium tuberculosis* having the sequence SEQ ID NO: 2.

* * * * *

SEQUENCE LISTING

```
<160> NUMBER OF SEQ ID NOS: 34

<210> SEQ ID NO 1
<211> LENGTH: 1691
<212> TYPE: DNA
<213> ORGANISM: Mycobacterium tuberculosis
<220> FEATURE:
<221> NAME/KEY: CDS
<222> LOCATION: (549)..(1562)

<400> SEQUENCE: 1
gatcatcatc ggccggctgc cgcgcagggc gccgacaccg gcgagtgcgg gcgcgaggat       60
cggcccccac cagttcggca gctgcgtgtc gatgcgctcc acaatcccgg gaaacagctc      120
gaccattacc tcctcaatat gagcctcgaa aaacttgccg ctgtgcgcgg cgtcgtggtg      180
agcgcacaca acaactgtta gctgaccagc aggatcggcg ctcttaccgg tctgttcacc      240
gcatatctga acggacggct gggagccacc cgcaagcaat tcatcgacta ctgcgtcaac      300
atgttgctca gcaccgccgc cacctacgca ccgcaccgcg agcggggaga atccgaacac      360
tccatcccag ccgggccgca caactgagga cgactggggt tcaccccacg cggccaccgg      420
ggcccgccga tgccagcatc ctgcccgctg ctggcagctc aacatgccgc gcgaagccca      480
aacttgatgc taccgagaga cacagatata ttgactgcaa ccattagaca cagataactg      540 gaggcgcc atg tca gcc aag ctg acc gac ctg cag ctg ctg cac gaa ctt       590
         Met Ser Ala Lys Leu Thr Asp Leu Gln Leu Leu His Glu Leu
           1               5                  10 gaa ccg gtc gtc gag aag tac ctg aac cgg cac ctg agc atg cac aag       638
Glu Pro Val Val Glu Lys Tyr Leu Asn Arg His Leu Ser Met His Lys
 15                  20                  25                  30 ccc tgg aac ccg cac gac tac atc ccg tgg tcg gac ggg aag aac tac       686
Pro Trp Asn Pro His Asp Tyr Ile Pro Trp Ser Asp Gly Lys Asn Tyr
                 35                  40                  45 tac gcg ctc ggc ggg cag gat tgg gac ccc gac cag agc aag ctt tct       734
Tyr Ala Leu Gly Gly Gln Asp Trp Asp Pro Asp Gln Ser Lys Leu Ser
```

-continued

```
                  50                      55                      60
gat gtc gcc cag gtg gcg atg gtg cag aac ctg gtc acc gag gac aac     782
Asp Val Ala Gln Val Ala Met Val Gln Asn Leu Val Thr Glu Asp Asn
        65                      70                      75 ctg ccg tcg tat cac cgc gag atc gcg atg aac atg ggc atg gac ggc     830
Leu Pro Ser Tyr His Arg Glu Ile Ala Met Asn Met Gly Met Asp Gly
        80                      85                      90 gcg tgg ggg cag tgg gtc aac cgt tgg acc gcc gag gag aat cgg cac     878
Ala Trp Gly Gln Trp Val Asn Arg Trp Thr Ala Glu Glu Asn Arg His
95                      100                     105                 110 ggc atc gcg ctg cgc gac tac ctg gtg gtg acc cga tcg gtc gac cct     926
Gly Ile Ala Leu Arg Asp Tyr Leu Val Val Thr Arg Ser Val Asp Pro
                115                     120                     125 gtc gag ttg gag aaa ctt cgc ctc gag gta gtc aac cgg ggc ttc agc     974
Val Glu Leu Glu Lys Leu Arg Leu Glu Val Val Asn Arg Gly Phe Ser
        130                     135                     140 cca ggc caa aac cac cag ggc cac tat ttc gcg gag agc ctc acc gac    1022
Pro Gly Gln Asn His Gln Gly His Tyr Phe Ala Glu Ser Leu Thr Asp
        145                     150                     155 tcc gtc ctc tat gtc agt ttc cag gaa ctg gca acc cgg att tcg cac    1070
Ser Val Leu Tyr Val Ser Phe Gln Glu Leu Ala Thr Arg Ile Ser His
        160                     165                     170 cgc aat acc ggc aag gca tgt aac gac ccc gtc gcc gac cag ctc atg    1118
Arg Asn Thr Gly Lys Ala Cys Asn Asp Pro Val Ala Asp Gln Leu Met
175                     180                     185                 190 gcc aag atc tcg gca gac gag aat ctg cac atg atc ttc tac cgc gac    1166
Ala Lys Ile Ser Ala Asp Glu Asn Leu His Met Ile Phe Tyr Arg Asp
                195                     200                     205 gtc agc gag gcc gcg ttc gac ctc gtg ccc aac cag gcc atg aag tcg    1214
Val Ser Glu Ala Ala Phe Asp Leu Val Pro Asn Gln Ala Met Lys Ser
        210                     215                     220 ctg cac ctg att ttg agc cac ttc cag atg ccc ggc ttc caa gta ccc    1262
Leu His Leu Ile Leu Ser His Phe Gln Met Pro Gly Phe Gln Val Pro
        225                     230                     235 gag ttc cgg cgc aaa gcc gtg gtc atc gcc gtc ggg ggt gtc tac gac    1310
Glu Phe Arg Arg Lys Ala Val Val Ile Ala Val Gly Gly Val Tyr Asp
        240                     245                     250 ccg cgc atc cac ctc gac gaa gtc gtc atg ccg gta ctg aag aaa tgg    1358
Pro Arg Ile His Leu Asp Glu Val Val Met Pro Val Leu Lys Lys Trp
255                     260                     265                 270 tgt atc ttc gag cgc gag gac ttc acc ggc gag ggg gct aag ctg cgc    1406
Cys Ile Phe Glu Arg Glu Asp Phe Thr Gly Glu Gly Ala Lys Leu Arg
                275                     280                     285 gac gag ctg gcc ctg gtg atc aag gac ctc gag ctg gcc tgc gac aag    1454
Asp Glu Leu Ala Leu Val Ile Lys Asp Leu Glu Leu Ala Cys Asp Lys
        290                     295                     300 ttc gag gtg tcc aag caa cgc caa ctc gac cgg gaa gcc cgt acg ggc    1502
Phe Glu Val Ser Lys Gln Arg Gln Leu Asp Arg Glu Ala Arg Thr Gly
        305                     310                     315 aag aag gtc agc gca cac gag ctg cat aaa acc gct ggc aaa ctg gcg    1550
Lys Lys Val Ser Ala His Glu Leu His Lys Thr Ala Gly Lys Leu Ala
320                     325                     330 atg agc cgt cgt tagcccggcg acgatgcaga gcgcgcagcg cgatgagcag         1602
Met Ser Arg Arg
335 gaggcgggca atccaaccca gcccggcgac gatgcagagc gcgcagcgcg atgagcagga   1662 ggtgggcaat ccaacccagc ccggcgttg                                    1691
```

<210> SEQ ID NO 2
<211> LENGTH: 338
<212> TYPE: PRT
<213> ORGANISM: Mycobacterium tuberculosis

<400> SEQUENCE: 2

Met Ser Ala Lys Leu Thr Asp Leu Gln Leu Leu His Glu Leu Glu Pro
1               5                   10                  15

Val Val Glu Lys Tyr Leu Asn Arg His Leu Ser Met His Lys Pro Trp
            20                  25                  30

Asn Pro His Asp Tyr Ile Pro Trp Ser Asp Gly Lys Asn Tyr Tyr Ala
        35                  40                  45

Leu Gly Gly Gln Asp Trp Asp Pro Asp Gln Ser Lys Leu Ser Asp Val
    50                  55                  60

Ala Gln Val Ala Met Val Gln Asn Leu Val Thr Glu Asp Asn Leu Pro
65                  70                  75                  80

Ser Tyr His Arg Glu Ile Ala Met Asn Met Gly Met Asp Gly Ala Trp
                85                  90                  95

Gly Gln Trp Val Asn Arg Trp Thr Ala Glu Glu Asn Arg His Gly Ile
            100                 105                 110

Ala Leu Arg Asp Tyr Leu Val Val Thr Arg Ser Val Asp Pro Val Glu
        115                 120                 125

Leu Glu Lys Leu Arg Leu Val Val Asn Arg Gly Phe Ser Pro Gly
    130                 135                 140

Gln Asn His Gln Gly His Tyr Phe Ala Glu Ser Leu Thr Asp Ser Val
145                 150                 155                 160

Leu Tyr Val Ser Phe Gln Glu Leu Ala Thr Arg Ile Ser His Arg Asn
                165                 170                 175

Thr Gly Lys Ala Cys Asn Asp Pro Val Ala Asp Gln Leu Met Ala Lys
            180                 185                 190

Ile Ser Ala Asp Glu Asn Leu His Met Ile Phe Tyr Arg Asp Val Ser
        195                 200                 205

Glu Ala Ala Phe Asp Leu Val Pro Asn Gln Ala Met Lys Ser Leu His
    210                 215                 220

Leu Ile Leu Ser His Phe Gln Met Pro Gly Phe Gln Val Pro Glu Phe
225                 230                 235                 240

Arg Arg Lys Ala Val Val Ile Ala Val Gly Gly Val Tyr Asp Pro Arg
                245                 250                 255

Ile His Leu Asp Glu Val Val Met Pro Val Leu Lys Lys Trp Cys Ile
            260                 265                 270

Phe Glu Arg Glu Asp Phe Thr Gly Glu Gly Ala Lys Leu Arg Asp Glu
        275                 280                 285

Leu Ala Leu Val Ile Lys Asp Leu Glu Leu Ala Cys Asp Lys Phe Glu
    290                 295                 300

Val Ser Lys Gln Arg Gln Leu Asp Arg Glu Ala Arg Thr Gly Lys Lys
305                 310                 315                 320

Val Ser Ala His Glu Leu His Lys Thr Ala Gly Lys Leu Ala Met Ser
                325                 330                 335

Arg Arg

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 3
cggcatatgt cagccaagct gaccgacctg cag        33

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ccgggatccc gcgctcgccg ctctgcatcg tcg        33

<210> SEQ ID NO 5
<211> LENGTH: 52
<212> TYPE: PRT
<213> ORGANISM: Epstein-barr virus

<400> SEQUENCE: 5

Glu Phe Tyr Lys Phe Leu Phe Thr Phe Leu Ala Met Ala Glu Lys Leu
 1               5                  10                  15

Val Asn Phe Asn Ile Asp Glu Leu Val Thr Ser Phe Glu Ser His Asp
                20                  25                  30

Ile Asp His Tyr Tyr Thr Glu Gln Lys Ala Met Glu Asn Val His Gly
            35                  40                  45

Glu Thr Tyr Ala
        50

<210> SEQ ID NO 6
<211> LENGTH: 52
<212> TYPE: PRT
<213> ORGANISM: Escherichia coli

<400> SEQUENCE: 6

Ile Phe Ile Ser Asn Leu Lys Tyr Gln Thr Leu Leu Asp Ser Ile Gln
 1               5                  10                  15

Gly Arg Ser Pro Asn Val Ala Leu Leu Pro Leu Ile Ser Ile Pro Glu
                20                  25                  30

Leu Glu Thr Trp Val Glu Thr Trp Ala Phe Ser Glu Thr Ile His Ser
            35                  40                  45

Arg Ser Tyr Thr
        50

<210> SEQ ID NO 7
<211> LENGTH: 52
<212> TYPE: PRT
<213> ORGANISM: Methylococcus capsulatus

<400> SEQUENCE: 7

Glu Thr Met Lys Val Val Ser Asn Phe Leu Glu Val Gly Glu Tyr Asn
 1               5                  10                  15

Ala Ile Ala Ala Thr Gly Met Leu Trp Asp Ser Ala Gln Ala Ala Glu
                20                  25                  30

Gln Lys Asn Gly Tyr Leu Ala Gln Val Leu Asp Glu Ile Arg His Thr
            35                  40                  45

His Gln Cys Ala
        50

```
<210> SEQ ID NO 8
<211> LENGTH: 52
<212> TYPE: PRT
<213> ORGANISM: Methylosinus trichosporium

<400> SEQUENCE: 8

Glu Thr Met Lys Val Ile Ser Asn Phe Leu Glu Val Gly Glu Tyr Asn
 1               5                  10                  15

Ala Ile Ala Ala Ser Ala Met Leu Trp Asp Ser Ala Thr Ala Ala Glu
            20                  25                  30

Gln Lys Asn Gly Tyr Leu Ala Gln Val Leu Asp Glu Ile Arg His Thr
        35                  40                  45

His Gln Cys Ala
        50

<210> SEQ ID NO 9
<211> LENGTH: 52
<212> TYPE: PRT
<213> ORGANISM: Pseudomonas sp.

<400> SEQUENCE: 9

Asn Ala Leu Lys Leu Phe Leu Thr Ala Val Ser Pro Leu Glu Tyr Gln
 1               5                  10                  15

Ala Phe Gln Gly Phe Ser Arg Val Gly Arg Gln Phe Ser Gly Ala Gly
            20                  25                  30

Ala Arg Val Ala Cys Gln Met Gln Ala Ile Asp Glu Leu Arg His Val
        35                  40                  45

Gln Thr Gln Val
        50

<210> SEQ ID NO 10
<211> LENGTH: 52
<212> TYPE: PRT
<213> ORGANISM: Pseudomonas mendocina

<400> SEQUENCE: 10

Ser Thr Leu Lys Ser His Tyr Gly Ala Ile Ala Val Gly Glu Tyr Ala
 1               5                  10                  15

Ala Val Thr Gly Glu Gly Arg Met Ala Arg Phe Ser Lys Ala Pro Gly
            20                  25                  30

Asn Arg Asn Met Ala Thr Phe Gly Met Met Asp Glu Leu Arg His Gly
        35                  40                  45

Gln Leu Gln Leu
        50

<210> SEQ ID NO 11
<211> LENGTH: 54
<212> TYPE: PRT
<213> ORGANISM: Ricinus communis

<400> SEQUENCE: 11

Leu Val Gly Asp Met Ile Thr Glu Glu Ala Leu Pro Thr Tyr Gln Thr
 1               5                  10                  15

Met Leu Asn Thr Leu Asp Gly Val Arg Asp Glu Thr Gly Ala Ser Pro
            20                  25                  30

Thr Ser Trp Ala Ile Trp Thr Arg Ala Trp Thr Ala Glu Glu Asn Arg
        35                  40                  45

His Gly Asp Leu Leu Asn
        50
```

<210> SEQ ID NO 12
<211> LENGTH: 54
<212> TYPE: PRT
<213> ORGANISM: Cucumis sativus

<400> SEQUENCE: 12

```
Leu Val Gly Asp Met Ile Thr Glu Glu Ala Leu Pro Thr Tyr Gln Thr
 1               5                  10                  15

Met Leu Asn Thr Leu Asp Gly Val Arg Asp Glu Thr Gly Ala Ser Pro
             20                  25                  30

Thr Pro Trp Ala Ile Trp Thr Arg Ala Trp Thr Ala Glu Glu Asn Arg
         35                  40                  45

His Gly Asp Leu Leu Asn
         50
```

<210> SEQ ID NO 13
<211> LENGTH: 54
<212> TYPE: PRT
<213> ORGANISM: Carthamus tinctorius

<400> SEQUENCE: 13

```
Leu Val Gly Asp Met Ile Thr Glu Glu Ala Leu Pro Thr Tyr Gln Thr
 1               5                  10                  15

Met Leu Asn Thr Leu Asp Gly Val Arg Asp Glu Thr Gly Ala Ser Leu
             20                  25                  30

Thr Pro Trp Ala Val Trp Thr Arg Ala Trp Thr Ala Glu Glu Asn Arg
         35                  40                  45

His Gly Asp Leu Leu His
         50
```

<210> SEQ ID NO 14
<211> LENGTH: 54
<212> TYPE: PRT
<213> ORGANISM: Spinacia oleracea

<400> SEQUENCE: 14

```
Leu Val Gly Asp Met Ile Thr Glu Glu Ala Leu Pro Thr Tyr Gln Thr
 1               5                  10                  15

Met Leu Asn Thr Leu Asp Gly Ala Lys Asp Glu Thr Gly Ala Ser Pro
             20                  25                  30

Thr Ser Trp Ala Val Trp Thr Arg Ala Trp Thr Ala Glu Glu Asn Arg
         35                  40                  45

His Gly Asp Leu Leu Asn
         50
```

<210> SEQ ID NO 15
<211> LENGTH: 54
<212> TYPE: PRT
<213> ORGANISM: Brassica sp.

<400> SEQUENCE: 15

```
Leu Val Gly Asp Met Ile Thr Glu Glu Ala Leu Pro Thr Tyr Gln Thr
 1               5                  10                  15

Met Leu Asn Thr Leu Asp Gly Val Arg Asp Glu Thr Gly Ala Ser Pro
             20                  25                  30

Thr Ser Trp Ala Ile Trp Thr Arg Ala Trp Thr Ala Glu Glu Asn Arg
         35                  40                  45

His Gly Asp Leu Leu Asn
```

<210> SEQ ID NO 16
<211> LENGTH: 54
<212> TYPE: PRT
<213> ORGANISM: Solanum tuberosum

<400> SEQUENCE: 16

Leu Ile Gly Asp Met Ile Thr Glu Glu Ala Leu Pro Thr Tyr Gln Thr
1               5                   10                  15

Met Ile Asn Thr Leu Asp Gly Val Arg Asp Glu Thr Gly Ala Thr Val
            20                  25                  30

Thr Pro Trp Ala Ile Trp Thr Arg Ala Trp Thr Ala Glu Glu Asn Arg
        35                  40                  45

His Gly Asp Leu Leu Asn
    50

<210> SEQ ID NO 17
<211> LENGTH: 54
<212> TYPE: PRT
<213> ORGANISM: Linum sp.

<400> SEQUENCE: 17

Leu Val Gly Asp Met Ile Thr Glu Glu Ala Leu Pro Thr Tyr Gln Thr
1               5                   10                  15

Met Leu Asn Thr Leu Asp Gly Val Arg Asp Glu Thr Gly Ala Ser Leu
            20                  25                  30

Thr Pro Trp Ala Ile Trp Thr Arg Ala Trp Thr Ala Glu Glu Asn Arg
        35                  40                  45

His Gly Asp Leu Leu Asn
    50

<210> SEQ ID NO 18
<211> LENGTH: 54
<212> TYPE: PRT
<213> ORGANISM: Coriandrum sativum

<400> SEQUENCE: 18

Leu Val Gly Asp Met Ile Thr Glu Glu Ala Leu Pro Thr Tyr Met Ser
1               5                   10                  15

Met Leu Asn Arg Cys Asp Gly Ile Lys Asp Thr Gly Ala Gln Pro
            20                  25                  30

Thr Ser Trp Ala Thr Trp Thr Arg Ala Trp Thr Ala Glu Glu Asn Arg
        35                  40                  45

His Gly Asp Leu Leu Asn
    50

<210> SEQ ID NO 19
<211> LENGTH: 52
<212> TYPE: PRT
<213> ORGANISM: Epstein-barr virus

<400> SEQUENCE: 19

Glu Lys Ile Leu Val Phe Leu Leu Ile Glu Gly Ile Phe Phe Ile Ser
1               5                   10                  15

Ser Phe Tyr Ser Ile Ala Leu Leu Arg Val Arg Gly Leu Met Pro Gly
            20                  25                  30

Ile Cys Leu Ala Asn Asn Tyr Ile Ser Arg Asp Glu Leu Leu His Thr
        35                  40                  45

-continued

Arg Ala Ser Ser
    50

<210> SEQ ID NO 20
<211> LENGTH: 52
<212> TYPE: PRT
<213> ORGANISM: Escherichia coli

<400> SEQUENCE: 20

Leu Cys Leu Met Ser Val Asn Ala Leu Glu Ala Ile Arg Phe Tyr Val
 1               5                  10                  15

Ser Phe Ala Cys Ser Phe Ala Phe Ala Glu Arg Glu Leu Met Glu Gly
            20                  25                  30

Asn Ala Lys Ile Ile Arg Leu Ile Ala Arg Asp Glu Ala Leu His Leu
        35                  40                  45

Thr Gly Thr Gln
    50

<210> SEQ ID NO 21
<211> LENGTH: 52
<212> TYPE: PRT
<213> ORGANISM: Methylococcus capsulatus

<400> SEQUENCE: 21

Cys Ser Leu Asn Leu Gln Leu Val Gly Glu Ala Cys Phe Thr Asn Pro
 1               5                  10                  15

Leu Ile Val Ala Val Thr Glu Trp Ala Ala Ala Asn Gly Asp Glu Ile
            20                  25                  30

Thr Pro Thr Val Phe Leu Ser Ile Glu Thr Asp Glu Leu Arg His Met
        35                  40                  45

Ala Asn Gly Tyr
    50

<210> SEQ ID NO 22
<211> LENGTH: 52
<212> TYPE: PRT
<213> ORGANISM: Methylosinus trichosporium

<400> SEQUENCE: 22

Cys Ser Val Asn Leu Gln Leu Val Gly Asp Thr Cys Phe Thr Asn Pro
 1               5                  10                  15

Leu Ile Val Ala Val Thr Glu Trp Ala Ile Gly Asn Gly Asp Glu Ile
            20                  25                  30

Thr Pro Thr Val Phe Leu Ser Val Glu Thr Asp Glu Leu Arg His Met
        35                  40                  45

Ala Asn Gly Tyr
    50

<210> SEQ ID NO 23
<211> LENGTH: 52
<212> TYPE: PRT
<213> ORGANISM: Pseudomonas sp.

<400> SEQUENCE: 23

Phe Leu Thr Ala Val Ser Phe Ser Phe Glu Tyr Val Leu Thr Asn Leu
 1               5                  10                  15

Leu Phe Val Pro Phe Met Ser Gly Ala Ala Tyr Asn Gly Asp Met Ala
            20                  25                  30

Thr Val Thr Phe Gly Phe Ser Ala Gln Ser Asp Glu Ala Arg His Met
        35                  40                  45

```
Thr Leu Gly Leu
     50

<210> SEQ ID NO 24
<211> LENGTH: 52
<212> TYPE: PRT
<213> ORGANISM: Pseudomonas mendocina

<400> SEQUENCE: 24

Val Ala Ile Met Leu Thr Phe Ser Phe Glu Thr Gly Phe Thr Asn Met
 1               5                  10                  15

Gln Phe Leu Gly Leu Ala Ala Asp Ala Ala Glu Ala Gly Asp Tyr Thr
             20                  25                  30

Phe Ala Asn Leu Ile Ser Ser Ile Gln Thr Asp Glu Ser Arg His Ala
         35                  40                  45

Gln Gln Gly Gly
     50

<210> SEQ ID NO 25
<211> LENGTH: 52
<212> TYPE: PRT
<213> ORGANISM: Ricinus communis

<400> SEQUENCE: 25

Tyr Leu Gly Phe Ile Tyr Thr Ser Phe Gln Glu Arg Ala Thr Phe Ile
 1               5                  10                  15

Ser His Gly Asn Thr Ala Arg Gln Ala Lys Glu His Gly Asp Ile Lys
             20                  25                  30

Leu Ala Gln Ile Cys Gly Thr Ile Ala Ala Asp Glu Lys Arg His Glu
         35                  40                  45

Thr Ala Tyr Thr
     50

<210> SEQ ID NO 26
<211> LENGTH: 52
<212> TYPE: PRT
<213> ORGANISM: Cucumis sativus

<400> SEQUENCE: 26

Tyr Leu Gly Phe Ile Tyr Thr Ser Phe Gln Glu Arg Ala Thr Phe Ile
 1               5                  10                  15

Ser His Gly Asn Thr Ala Arg Leu Ala Lys Glu His Gly Asp Ile Lys
             20                  25                  30

Leu Ala Gln Ile Cys Gly Thr Ile Thr Ala Asp Glu Lys Arg His Glu
         35                  40                  45

Thr Ala Tyr Thr
     50

<210> SEQ ID NO 27
<211> LENGTH: 52
<212> TYPE: PRT
<213> ORGANISM: Carthamus tinctorius

<400> SEQUENCE: 27

Tyr Leu Gly Phe Ile Tyr Thr Ser Phe Gln Glu Arg Ala Thr Phe Val
 1               5                  10                  15

Ser His Gly Asn Thr Ala Arg His Ala Lys Asp His Gly Asp Val Lys
             20                  25                  30

Leu Ala Gln Ile Cys Gly Thr Ile Ala Ser Asp Glu Lys Arg His Glu
```

```
                35                  40                  45

Thr Ala Tyr Thr
    50

<210> SEQ ID NO 28
<211> LENGTH: 52
<212> TYPE: PRT
<213> ORGANISM: Spinacia oleracea

<400> SEQUENCE: 28

Tyr Leu Gly Phe Val Tyr Thr Ser Phe Gln Glu Arg Ala Thr Phe Val
  1               5                  10                  15

Ser His Gly Asn Ser Ala Arg Leu Ala Lys Glu His Gly Asp Leu Lys
                20                  25                  30

Met Ala Gln Ile Cys Gly Ile Ile Ala Ser Asp Glu Lys Arg His Glu
            35                  40                  45

Thr Ala Tyr Thr
    50

<210> SEQ ID NO 29
<211> LENGTH: 52
<212> TYPE: PRT
<213> ORGANISM: Brassica sp.

<400> SEQUENCE: 29

Tyr Leu Gly Phe Ile Tyr Thr Ser Phe Gln Glu Arg Ala Thr Phe Ile
  1               5                  10                  15

Ser His Gly Asn Thr Ala Arg Gln Ala Lys Glu His Gly Asp Leu Lys
                20                  25                  30

Leu Ala Gln Ile Cys Gly Thr Ile Ala Ala Asp Glu Lys Arg His Glu
            35                  40                  45

Thr Ala Tyr Thr
    50

<210> SEQ ID NO 30
<211> LENGTH: 52
<212> TYPE: PRT
<213> ORGANISM: Solanum tuberosum

<400> SEQUENCE: 30

Tyr Leu Gly Phe Val Tyr Thr Ser Leu Arg Lys Gly Val Thr Phe Val
  1               5                  10                  15

Ser His Gly Asn Thr Ala Arg Leu Ala Lys Glu His Gly Asp Met Lys
                20                  25                  30

Leu Ala Gln Ile Cys Gly Ser Ile Ala Ala Asp Glu Lys Arg His Glu
            35                  40                  45

Thr Ala Tyr Thr
    50

<210> SEQ ID NO 31
<211> LENGTH: 52
<212> TYPE: PRT
<213> ORGANISM: Linum sp.

<400> SEQUENCE: 31

Tyr Leu Gly Phe Ile Tyr Thr Ser Phe Gln Glu Arg Ala Thr Phe Ile
  1               5                  10                  15

Ser His Gly Asn Thr Ala Arg Leu Ala Lys Asp His Gly Asp Met Lys
                20                  25                  30
```

```
Leu Ala Gln Ile Cys Gly Ile Ile Ala Ala Asp Glu Lys Arg His Glu
        35                  40                  45

Thr Ala Tyr Thr
    50

<210> SEQ ID NO 32
<211> LENGTH: 52
<212> TYPE: PRT
<213> ORGANISM: Coriandrum sativum

<400> SEQUENCE: 32

Tyr Met Gly Phe Ile Tyr Thr Ser Phe Gln Glu Arg Ala Thr Phe Ile
 1               5                  10                  15

Ser His Ala Asn Thr Ala Lys Leu Ala Gln His Tyr Gly Asp Lys Asn
            20                  25                  30

Leu Ala Gln Val Cys Gly Asn Ile Ala Ser Asp Glu Lys Arg His Ala
        35                  40                  45

Thr Ala Tyr Thr
    50

<210> SEQ ID NO 33
<211> LENGTH: 54
<212> TYPE: PRT
<213> ORGANISM: Mycobacterium tuberculosis

<400> SEQUENCE: 33

Ser Asp Val Ala Gln Val Ala Met Val Gln Asn Leu Val Thr Glu Asp
 1               5                  10                  15

Asn Leu Pro Ser Tyr His Arg Glu Ile Ala Met Asn Met Gly Met Asp
            20                  25                  30

Gly Ala Trp Gly Gln Trp Val Asn Arg Trp Thr Ala Glu Glu Asn Arg
        35                  40                  45

His Gly Ile Ala Leu Arg
    50

<210> SEQ ID NO 34
<211> LENGTH: 49
<212> TYPE: PRT
<213> ORGANISM: Mycobacterium tuberculosis

<400> SEQUENCE: 34

Thr Asp Ser Val Leu Tyr Val Ser Phe Gln Glu Leu Ala Thr Arg Ile
 1               5                  10                  15

Ser His Arg Asn Thr Gly Lys Ala Cys Asn Asp Pro Val Ala Asp Gln
            20                  25                  30

Leu Met Ala Lys Ile Ser Ala Asp Glu Asn Leu His Met Ile Phe Tyr
        35                  40                  45

Arg
```